(12) United States Patent
Acharya et al.

(10) Patent No.: US 10,967,066 B2
(45) Date of Patent: Apr. 6, 2021

(54) STAPLED ACID-SENSITIVE ENDOSOME DISRUPTING ALGINATES

(71) Applicant: University of Pittsburgh—Of the Commonwealth System of Higher Education, Pittsburgh, PA (US)

(72) Inventors: Abhinav Acharya, Pittsburgh, PA (US); Stephen R. Little, Allison Park, PA (US)

(73) Assignee: University of Pittsburgh—Of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 16/450,553

(22) Filed: Jun. 24, 2019

(65) Prior Publication Data
US 2019/0307889 A1    Oct. 10, 2019

Related U.S. Application Data

(62) Division of application No. 15/580,646, filed as application No. PCT/US2016/039873 on Jun. 28, 2016, now Pat. No. 10,376,592.

(60) Provisional application No. 62/186,141, filed on Jun. 29, 2015.

(51) Int. Cl.
| | | |
|---|---|---|
| *C08L 5/04* | (2006.01) | |
| *A61K 47/61* | (2017.01) | |
| *A61K 31/734* | (2006.01) | |
| *C08B 37/00* | (2006.01) | |
| *A61K 31/30* | (2006.01) | |
| *A61P 25/28* | (2006.01) | |
| *A61P 35/00* | (2006.01) | |
| *A61K 9/06* | (2006.01) | |
| *A61K 9/50* | (2006.01) | |
| *A61K 33/34* | (2006.01) | |
| *A61K 41/00* | (2020.01) | |
| *A61K 45/06* | (2006.01) | |

(52) U.S. Cl.
CPC .......... *A61K 47/61* (2017.08); *A61K 9/06* (2013.01); *A61K 9/5036* (2013.01); *A61K 31/30* (2013.01); *A61K 31/734* (2013.01); *A61K 33/34* (2013.01); *A61K 41/0028* (2013.01); *A61K 45/06* (2013.01); *A61P 25/28* (2018.01); *A61P 35/00* (2018.01); *C08B 37/0084* (2013.01); *C08L 5/04* (2013.01)

(58) Field of Classification Search
CPC ...... A61K 9/06; A61K 9/5036; A61K 31/734; A61K 31/30; A61K 45/06; A61K 47/61; C08L 5/04; C08B 37/0084
USPC ........................................................ 424/493
See application file for complete search history.

(56) References Cited

U.S. PATENT DOCUMENTS

| | | |
|---|---|---|
| 4,948,575 A | 8/1990 | Cole et al. |
| 6,642,363 B1 | 11/2003 | Mooney et al. |
| 8,741,872 B2 * | 6/2014 | Melvik .............. A61L 27/3641 514/54 |
| 2010/0210504 A1 | 8/2010 | Hoffman et al. |

FOREIGN PATENT DOCUMENTS

| | | |
|---|---|---|
| EP | 0 849 281 | 6/1998 |
| WO | WO 94/07536 | 4/1994 |

OTHER PUBLICATIONS

Singh, et al; title: Hydrogels and Scaffolds for Immunomodulation; Advanced Materials, vol. 26, Issue38, Oct. 15, 2014; pp. 6530-6541; first published: Aug. 25, 2014. (Year: 2014).*
Bikram et al, title: Thermo-responsive systems for controlled drug delivery; Expert Opinion on Drug Delivery; vol. 5, Issue 10; pp. 1077-1091; published online: Sep. 25, 2008. (Year: 2008).*
Binauld, "Acid-degradable polymers for drug delivery: a decade of innovation," *Chem. Commun.*, 49(21): 2082-102, Mar. 14, 2013.
Chan et al., "Tuneable semi-synthetic network of alginate for absorptive encapsulation and controlled release of protein therapeutics," *Biomaterials*, vol. 31, pp. 9040-9047, Aug. 23, 2010.
Chan et al., "Modeling the controllable pH-responsive swelling and pore size of networked alginate based biomaterials," *Biomaterials*, vol. 30, pp. 6119-6129, Aug. 5, 2009.
Chan et al., "Kinetic Controlled Synthesis of pH-responsive network alginate," *Biomacromolecules*, vol. 9, pp. 2536-2545, Jul. 31, 2008.
Das et al., "Zinc alginate-carboxymethyl cashew gum microbeads for prolonged drug release: development and optimization," *International Journal of Biological Macromolecules*, vol. 70, pp. 506-515, Sep. 18, 2016.
Klinkajon et al., "Novel copper (II) alginate hydrogels and their potential for use as anti-bacterial wound dressings," *Biomed. Mater.*, 9(4): Jul. 16, 2014.
Lee et al., "Alginate: properties and biomedical applications," *Progress in Polymer Science*, 37(1): 106-126, Jan. 2012.
Matricardi et al., "Recent advances and perspectives on coated alginate microspheres for modified drug delivery," *Expert Opinion on Drug Delivery*, 5(4): 417-425, Apr. 21, 2008.
Narayanan et al., "Photodegradable iron (III) cross-linked alginate gels," *Biomacromolecules*, 13(8): 2465-2471, Jul. 9, 2012.
Timar et al., "Oral administration of a trace element preparation and zinc inhibit liver metastasis of 3LL-HH murine tumor cells," *International Journal of Molecular Medicine*, vol. 2, pp. 105-108, Jul. 1, 1998.
Ummarino et al., "Effect of magnesium alginate plus simethicone on gastroesophageal reflux in infants," *Journal of Pediatric Gastroenterology and Nutrition*, 60(2): 230-235, Feb. 2015.

* cited by examiner

*Primary Examiner* — Yanzhi Zhang
(74) *Attorney, Agent, or Firm* — Klarquist Sparkman, LLP

(57) ABSTRACT

An agent comprising:
   an algin crosslinked with acetal linkages; and
   at least one cation coupled to the crosslinked algin.

21 Claims, 8 Drawing Sheets

STAPLED ACID-SENSITIVE ENDOSOME DISRUPTING ALGINATES

CROSS-REFERENCE TO RELATED APPLICATION

This application is a divisional of U.S. application Ser. No. 15/580,646, filed Dec. 7, 2017, which is the U.S. National Stage of International Application No. PCT/US2016/039873, filed Jun. 28, 2016, which was published in English under PCT Article 21(2), which in turn claims the benefit of U.S. Provisional Application No. 62/186,141, filed Jun. 29, 2015, which application is incorporated herein by reference in its entirety.

BACKGROUND

Cations such as calcium, copper, iron, zinc, and magnesium among others are the most abundant minerals and are essential in several signaling pathways in all biological systems. Both eukaryotic and prokaryotic cells are efficient in maintaining optimum levels of minerals in the cytosol, and therefore, selectively increasing the intracellular levels of minerals in order to modulate the cytosolic signaling pathways has been challenging. For example, intracellular Cu to Zn ratio is maintained and utilized by enzymes such as catalase to prevent accumulation of excess hydrogen peroxide, and superoxide dismutase to prevent excess accumulation of radical oxygen. Disrupting this mineral homeostasis has been demonstrated to be effective in inducing cell death selectively in cancer cells as compared to non-cancerous cells. For example, superoxide mimics, such as copper(II) (3,5-diisopropylsalicylate)$_2$ (Cu(II)DIPS) have been shown to induce hydrogen peroxide accumulation due to the conversion of radical oxygen into hydrogen peroxide, with this accumulation of hydrogen peroxide leading to cell death in cancer cells. Conversely, given that relatively low levels of superoxide are generated in normal cells, increasing the levels of hydrogen peroxide in non-cancerous cells can lead to their proliferation and survival. Currently, delivery of cell permeable Cu (II) requires the use of solvents such as dimethyl sulfoxide (DMSO) or ethanol and therefore making the formulation not particularly suitable for clinical translation. Therefore, there remains a need for development of effective delivery vehicles for cations, such as Cu (II), to the cytosol of the cells.

SUMMARY

Disclosed herein are endosome disrupting polymer alginoketals that can be formulated into particles, and deliver any cation to the cytosol of the cells, thereby modulating their functions.

Disclosed herein is an agent comprising:
an algin crosslinked with acetal linkages; and
at least one cation coupled to the crosslinked algin.
Also disclosed herein is an agent comprising:
an algin monosaccharide residue covalently bonded to an acetal group forming an alginoketal; and
at least one cation coupled to the alginoketal.
Further disclosed herein is an agent having a structure comprising:

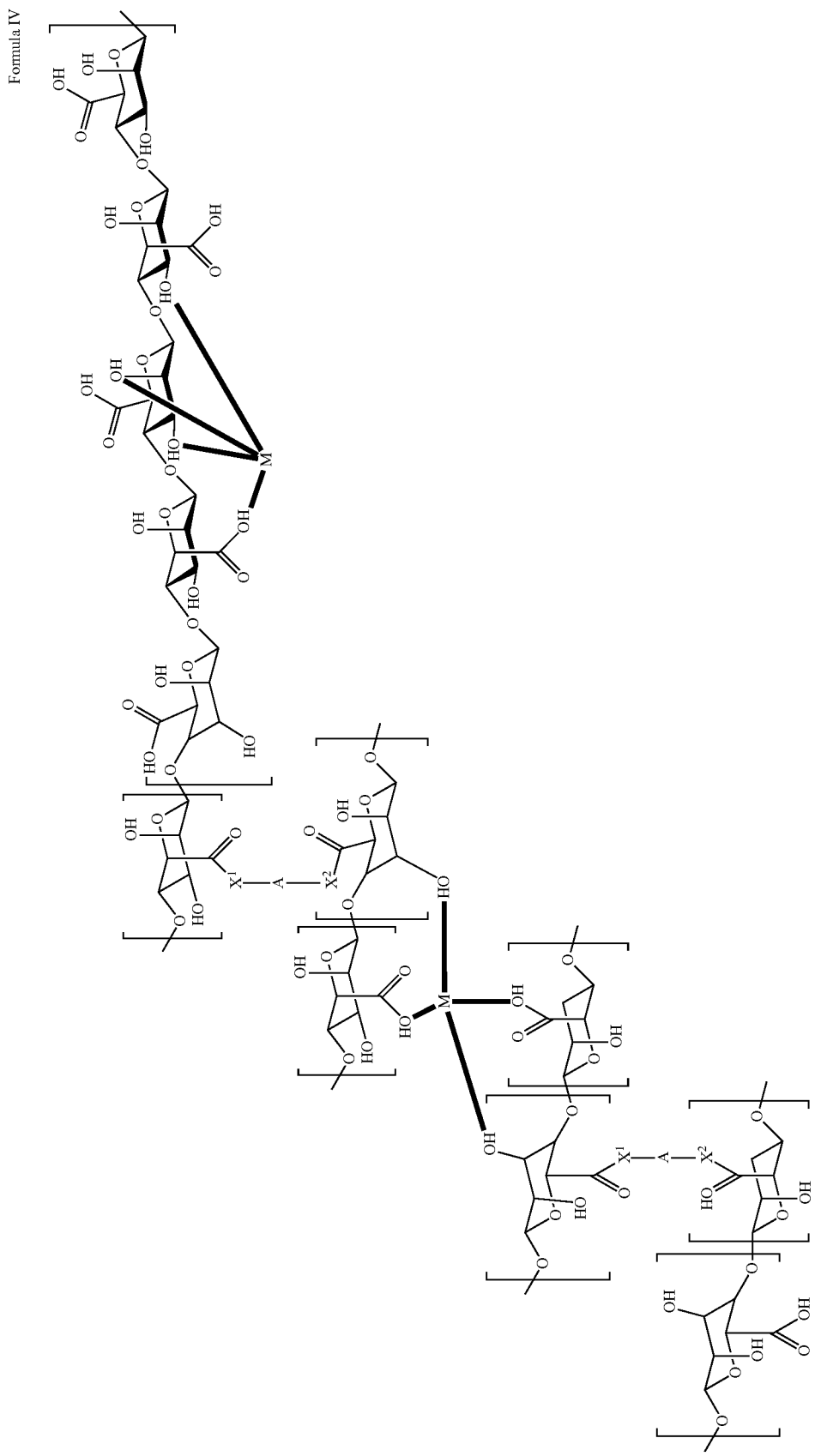

wherein M is a cation; $X^1$ and $X^2$ are each independently —NH— or —O—, and A includes an acetal group;

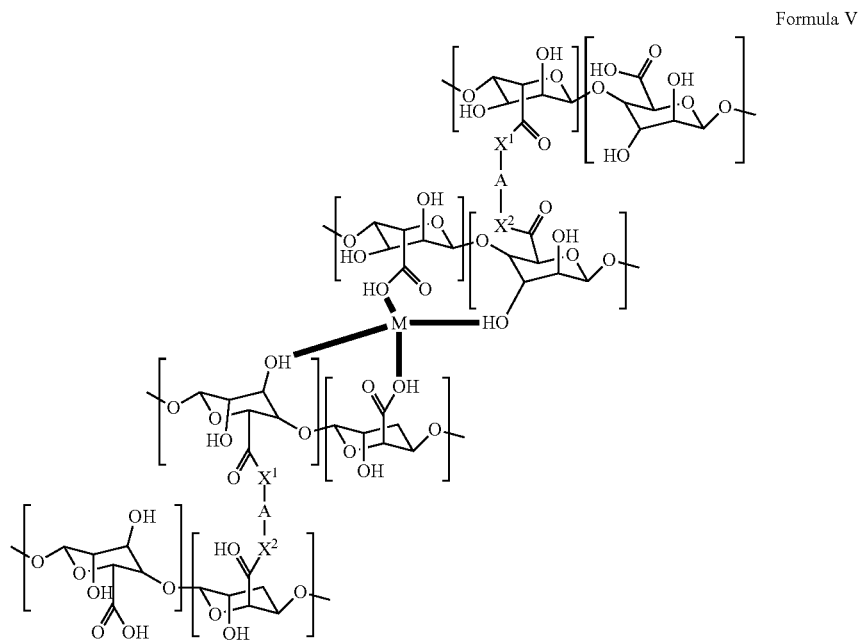

Formula V wherein M is a cation; $X^1$ and $X^2$ are each independently —NH— or —O—, and A includes an acetal group;
or a combination of Formula IV and Formula V.

The foregoing will become more apparent from the following detailed description, which proceeds with reference to the accompanying figures.

BRIEF DESCRIPTION OF THE DRAWINGS

(FIG. 6A) Mice were injected with $0.5 \times 10^5$ B16F10-OVA expressing cells in the right and left flank of mice (shown in blue), and when the tumors were palpable alginoketal particles mixed with thermoresponsive gel as described in the Example below were injected in the periphery of one of the tumors. (FIG. 6B) Kaplan Meier survival curves were obtained after treatment with particles till day 28. Tumor growth was measured in the (FIG. 6C) ipsilateral and (FIG. 6D) contralateral side after treatment for 28 days using calipers. The tumor size for different treatment groups was plotted against days and compared.

DETAILED DESCRIPTION

Overview

Figure 1:
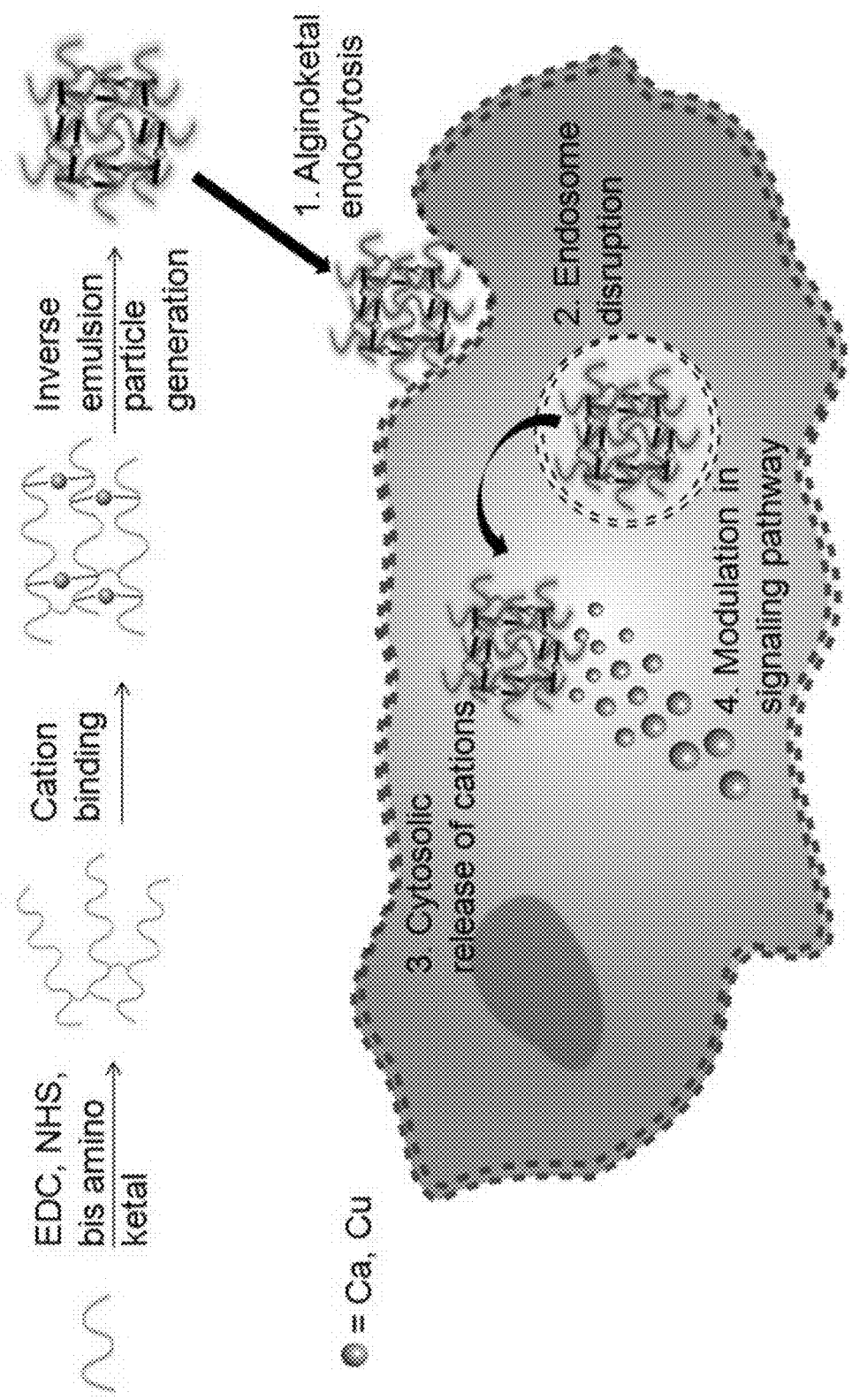
FIG. 1: Alginoketals deliver cations to the cytosol of the cells for modulating the cytosolic signaling pathways. Alginoketals have endosome disrupting capability, and are held together, at least in part, by cations as the binding agent. Upon endocytosis, alginoketals disrupt the endosome and release cations in a sustained manner thereby modulating intracellular signaling pathways.

Divalent cations, the most prevalent minerals in the body are responsible for a wide variety of cellular functions including signaling, proliferation, differentiation and cell death, and therefore their transmembrane transportation is tightly regulated. Several of the divalent cations such as Cu and Fe are toxic to the cells, and therefore, their homeostasis is regulated through a system of membrane bound protein transporters. For example, membrane transport protein Ctrl regulates the amount of Cu transported into the cells. Cations, such as Cu and Zn are indispensable to the function of various cytosolic signaling pathways and enzymes, and therefore, modulating their levels in the cytosol is attractive. However, due to the tight regulation of these cations, increasing the intracellular levels of cations is a challenge. Despite the importance of divalent cations in cell activity, there are currently no intracellular delivery methods for divalent cations or modulation of intracellular levels of minerals.

Described herein are endosome disrupting alginate nanoparticles termed "alginoketals," which can deliver cations to the cytosol of the cells. Alginoketals are generated by crosslinking alginic acid with endosome disrupting ketals, and using cations as the stapling or binding agent. For example, alginoketals are able to deliver copper (II) in the cytosol of the cancer cells thereby disrupting copper homeostasis and inducing cell death via accumulation of hydrogen peroxide. Alginoketal-copper (II) based particles act as superoxide dismutase mimics and are the first class of divalent cation delivery vehicles, with potential application in cancer therapy, regenerative medicine and drug delivery.

The polymers disclosed herein are excellent for delivering cations, because of their inherent capacity to chelate cations. Notably, alginoketal particles can be generated by intercalating cations within an alginate matrix, and therefore, can capture, for example, Ca, Zn, Fe, Cu and Mg. Nanoparticles could be generated from these polymers using an inverse emulsion resulting in endocytosable delivery vehicles for Cu (II) and other cations. This is significant because, until now, delivery of Cu (II), has required the use of hydrophobic chelators such as Cu(II)DIPS, which (in turn) require organic solvents for delivery. Therefore, biodegradable alginoketal particles represent a new and more translatable organic solvent-free option for delivering cations such as Cu (II).

The endosome disrupting ability of alginoketal polymers is demonstrated herein. Low pH-driven hydrolysis of the ketal or acetal linkages in the alginoketal particle can induce osmotic swelling of the endosomes and therefore, lead to its disruption. Although, ketal linkages have previously been utilized to generate drug delivery vehicles, the previous polymers cannot be utilized to deliver cations because of their inability to chelate cations. On the other hand, alginoketal particles are the only endosome disrupting polymers that can chelate cations, and therefore, are an excellent resource for divalent cation delivery to the cytosol of the cells. We demonstrate that Cu (II) (which is a binding agent of alginoketal particles) can be delivered to the cytosol of the cells. Once in the cytosol, alginoketal-Cu particles act as a superoxide dismutase mimic and can generate hydrogen peroxide from superoxides, which modulates cell function. Notably, superoxide dismutase mimics such as Cu(II)DIPS have been shown to be effective in clearing tumors in mice. Accordingly, the in vitro experiments disclosed herein suggest that alginoketal-Cu administration leads to M05 melanoma cell death. This can be attributed to the accumulation of hydrogen peroxide. Non-cancerous cells produce substantially less superoxide than cancer cells, and therefore, it is expected that the accumulation of hydrogen peroxide, due to superoxide dismutase mimics, in non-cancerous cells will not cause substantial cell death.

In certain embodiments:
- Alginoketals can also be made positively charged and thereby target the negatively charged surfaces such as cell surfaces and biofilms among others without being cytotoxic;
- The alginoketal is acid-sensitive, that is it degrades faster in the presence of acid than in the presence of physiologic pH;
- The alginoketal is the first class of particles that can deliver cations such as, copper(II), iron(II), calcium(II) zinc (II) among others.
- The alginoketals can encapsulate an immunotherapeutic agent and/or cancer cytotoxic agent.

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration" as used herein is inclusive of administration by another person to the subject or self-administration by the subject.

"Algins" as used herein includes alginic acid and salts or esters of alginic acid, irrespective of the relative proportion of mannuronic and guluronic units, and is intended to include glycolated or alkoxylated derivatives. Algins may be found in and isolated from various organisms, in particular from algae belonging to the order Phaeophyceae and soil bacteria such as *Azotobacter vinelandii* and *Azotobacter crococcum* and from several strains of *Pseudomonas* bacteria. Common algal sources of algins include *Laminaria digitata, Ecklonia maxima, Macrocystis pyrifera, Lessonia nigrescens, Ascophyllum nodosum, Laminaria japonica, Durvillea antartica, Durvillea potatorum* and, especially, *Laminaria hyperborea*. Alginic acid is a linear heteropolysaccharide comprising units of β-D-mannuronic acid and α-L-guluronic acid. Alginic acid may comprise homopolymeric sequences of mannuronic acid, homopolymeric sequences of guluronic acid, and mixed sequences of mannuronic acid and guluronic acid units.

The term "aliphatic" is defined as including alkyl, alkenyl, alkynyl, halogenated alkyl and cycloalkyl groups. A "lower aliphatic" group is a branched or unbranched aliphatic group having from 1 to 10 carbon atoms.

"Alkanediyl" refers to a divalent radical derived from aliphatic hydrocarbons.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-c_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Inhibiting" refers to inhibiting the full development of a disease or condition. "Inhibiting" also refers to any quantitative or qualitative reduction in biological activity or binding, relative to a control.

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as cancer. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, C.sub.1-4 alkyl, or C.sub.1-4 alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Prodrugs of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. F or a general discussion of prodrugs involving esters see Svensson and Tunek, *Drug Metabolism Reviews* 165 (1988) and Bundgaard, Design of Prodrugs, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed agents may include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized in or are purified to be in substantially enantiopure form, such as in a 90% enantiomeric excess, a 95% enantiomeric excess, a 97% enantiomeric excess or even in greater than a 99% enantiomeric excess, such as in enantiopure form.

The presently disclosed agents can have at least one asymmetric center or geometric center, cis-trans center (C=C, C=N). All chiral, diastereomeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}$F, etc.

Alginoketals and Alginoketal-M Agents

Disclosed herein are polymers, agents, compositions and methods for transporting or releasing therapeutic and diagnostic agents or metabolites or other analytes from cells, compartments within cells, through cell layers or cell barriers, or lipid membranes. The polymers, agents or compositions are endosomal disruptive materials that become membrane disruptive following endocytosis, releasing a therapeutic, diagnostic or prophylactic agent for delivery.

The endosomal disruptive materials are disrupted upon exposure to an appropriate stimulus, typically a change in pH, and most typically a decrease in pH from physiological pH (i.e., typically pH 7.4) to the pH of the endosome (approximately between 5 and 6.5). The endosomal disruptive materials include an acid labile acetal linkage which is cleaved following or during endocytosis.

The alginoketal includes an algin component(s) directly linked to a ketal component(s). The direct linkage preferably is via a covalent bond. In certain embodiments, the ketal component(s) forms an acetal linkage between algin polymer chains or within the same algin polymer chain. The acetal linking group may crosslink and/or chain extend the algin polymer chains. In certain embodiments, the acetal linking group is bonded to a carboxyl group present on an algin monosaccharide residue. In certain embodiments, the algin is directly conjugated to the ketal. In other words, there are no spacers or any other components in the alginoketal backbone structure. Examples of alginoketal structures are shown in FIGS. 1 and 2 and below:

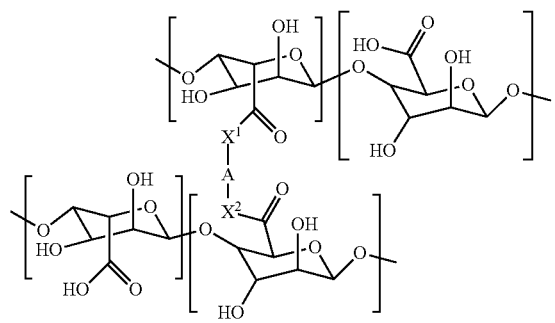

Formula I wherein $X^1$ and $X^2$ are each independently —NH— or —O—, and A includes an acetal group. More particularly, A is

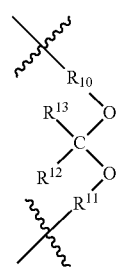

wherein $R^{10}$ and $R^{11}$ are each independently an alkanediyl, and $R^{12}$ and $R^{11}$ are each optionally substituted alkyl.

In certain embodiments, $X^1$ and $X^2$ are the same.

In certain embodiments, $R^{10}$ and $R^{11}$ are the same, and are particularly $(C_1-C_6)$alkanediyl.

In a further embodiment, the alginoketal includes a structure of:

Formula II

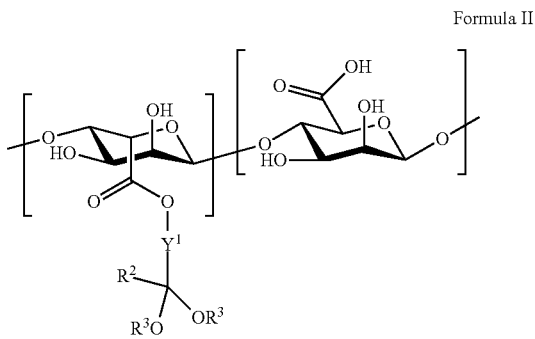

wherein $Y^1$ is an alkanediyl, $R^2$ is optionally substituted alkyl, and each $R^3$ is independently optionally substituted alkyl or an algin monosaccharide residue. In certain embodiments, at least one $R^3$ is an algin monosaccharide residue.

In a specific embodiment, the alginoketal includes a structure of:

Formula III

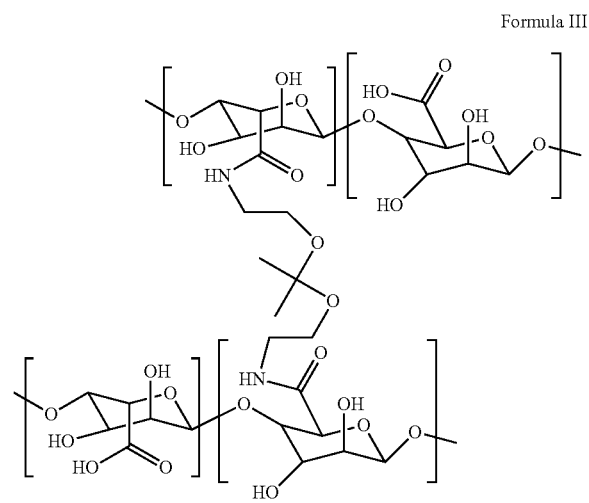

Alginic acid itself may be used the presently disclosed methods as a starting material for making the alginoketals. However, salts of alginic acid may also be used in the methods and may include alkali metal salts, for example sodium and potassium salts, and ammonium and alkanolamine salts. Esters of alginic acid may also be used in the methods provided there is a sufficient number of free carboxyl groups available for conjugating with the ketal. The algin starting material is the precursor for the algin monosaccharide residues present in the alginoketal.

The ketal used to make the alginoketal may be any compound that includes at least one ketal group and at least one functional group that is reactive with a carboxyl group or a hydroxyl group present on an algin monosaccharide residue. In certain embodiments, the ketal includes an amine group that is reactive with the carboxyl group thus generating an amide linkage. In certain embodiments, the ketal includes a hydroxyl group that is reactive with the carboxyl group thus generating an ester linkage. In certain embodiments, the ketal includes a halogen group that is reactive with the hydroxyl group of the algin monosaccharide residue. Illustrative ketals include 2,2-bis(aminoethoxy)propane, 1-(2-Hydroxyethyl)-4-piperidone ethylene ketal, 1-Amino-4-oxocyclohexanecarboxylic acid ethylene ketal, and 4-Bromoacetophenone diethyl ketal.

In certain embodiments, a ketone could be introduced onto the algin polymer, and then converted to a ketal.

A divalent cation may be coupled to the alginoketal. In certain embodiments, the cation may be a metal cation or non-metal cation. Illustrative cations include copper (II), iron (II), calcium (II), zinc (II), magnesium (II), selenium, aluminium, manganese, barium, and strontium. A cation-bearing compound is contacted with the alginoketal under conditions for coupling the cation with the alginoketal. The cation-bearing compound may be a salt of the above-identified divalent cations. Illustrative salts include sulfate, phosphate, chloride, bromide, fluoride, and pyrophosphate.

Certain embodiments disclosed herein are the first class of polymers that can deliver several different kinds of cations simultaneously. In other words, a single molecule of alginoketal can be loaded with more than one type of cation (e.g., Cu(II) and Ca(II)). The amount of cations per alginoketal may vary. For example, the cation content may range from 1 picomole to 1 mole, more particularly 1 nanomole to 1 micromole, and most particularly 1 nanomole to 100 nanomole.

In certain embodiments, the cation is chelated to the alginoketal. For example, in certain embodiments, the cation is covalently or ionic bonded to a carboxyl and/or hydroxyl group present on the alginoketal. Illustrative examples of alginoketal-cation structures are shown in are shown in FIG. 1 and below.

For example, the alginoketal-cation may include a structure of:

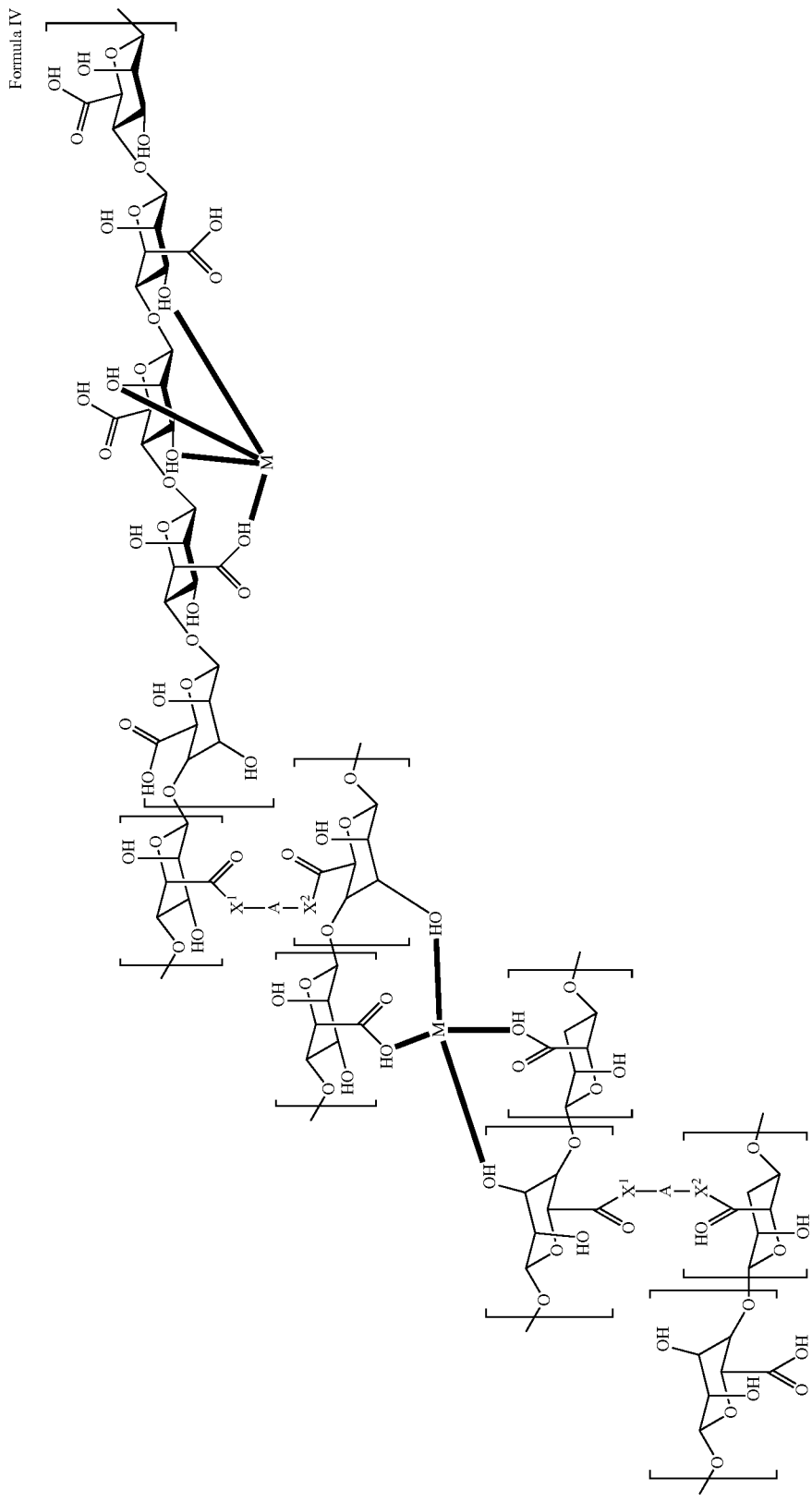
Formula IV wherein M is a cation; $X^1$ and $X^2$ are each independently —NH— or —O—, and A includes an acetal group. More particularly, A is

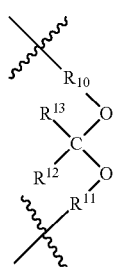

wherein $R^{10}$ and $R^{11}$ are each independently an alkanediyl, and $R^{12}$ and $R^{13}$ are each optionally substituted alkyl.

In certain embodiments, $X^1$ and $X^2$ are the same.

In certain embodiments, $R^{10}$ and $R^{11}$ are the same, and are particularly ($C_1$-C6)alkanediyl.

In a further example, the alginoketal-cation may include a structure of:

wherein M is a cation; $X^1$ and $X^2$ are each independently —NH— or —O—, and A includes an acetal group. More particularly, A is

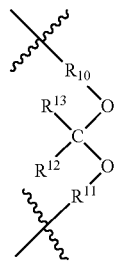

wherein $R^{10}$ and $R^{11}$ are each independently an alkanediyl, and $R^{12}$ and $R^{13}$ are each optionally substituted alkyl.

In certain embodiments, $X^1$ and $X^2$ are the same.

In certain embodiments, $R^{10}$ and $R^{11}$ are the same, and are particularly ($C_1$-C6)alkanediyl.

In a further example, the alginoketal-cation may include a structure of:

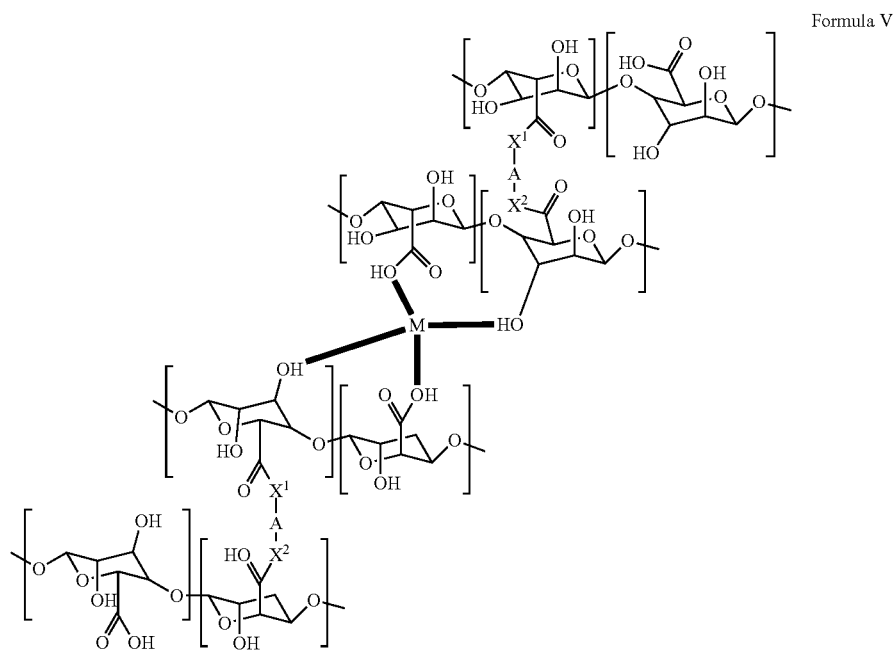

Formula V

Formula VI

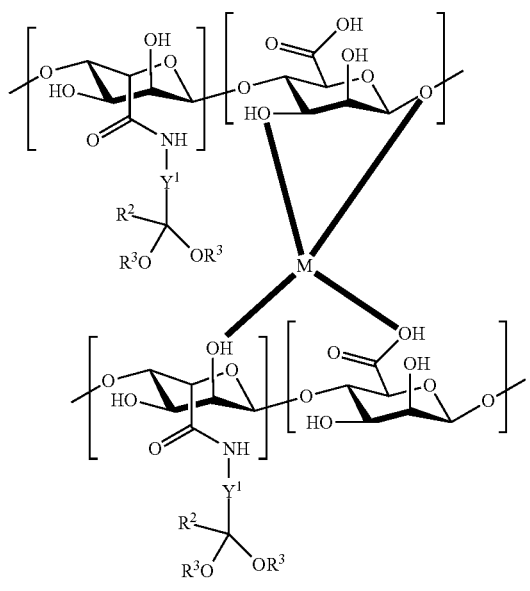

wherein M is a cation, $Y^1$ is an alkanediyl, $R^2$ is optionally substituted alkyl, and each $R^3$ is independently optionally substituted alkyl or an algin monosaccharide residue, provided that at least one of $R^3$ is an algin monosaccharide residue.

In a further example, the alginoketal-cation may include a structure of:

Formula VII

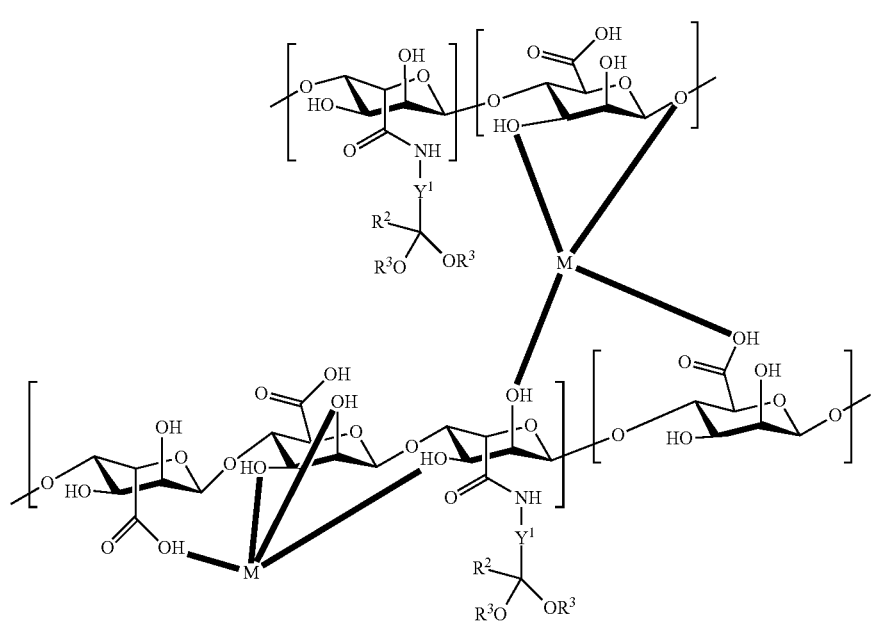

wherein M is a divalent cation, $Y^1$ is an alkanediyl, $R^2$ is optionally substituted alkyl, and each $R^3$ is independently optionally substituted alkyl or an algin monosaccharide residue, provided that at least one of $R^3$ is an algin monosaccharide residue.

In a further example, the alginoketal-cation may include a structure of:

Formula VIII

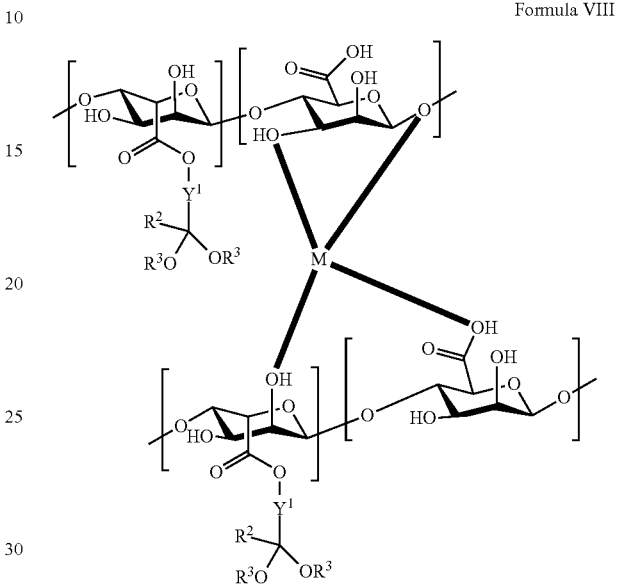

wherein M is a divalent cation, $Y^1$ is an alkanediyl, $R^2$ is optionally substituted alkyl, and each $R^3$ is independently optionally substituted alkyl or an algin monosaccharide residue, provided that at least one of $R^3$ is an algin monosaccharide residue.

Formula IX

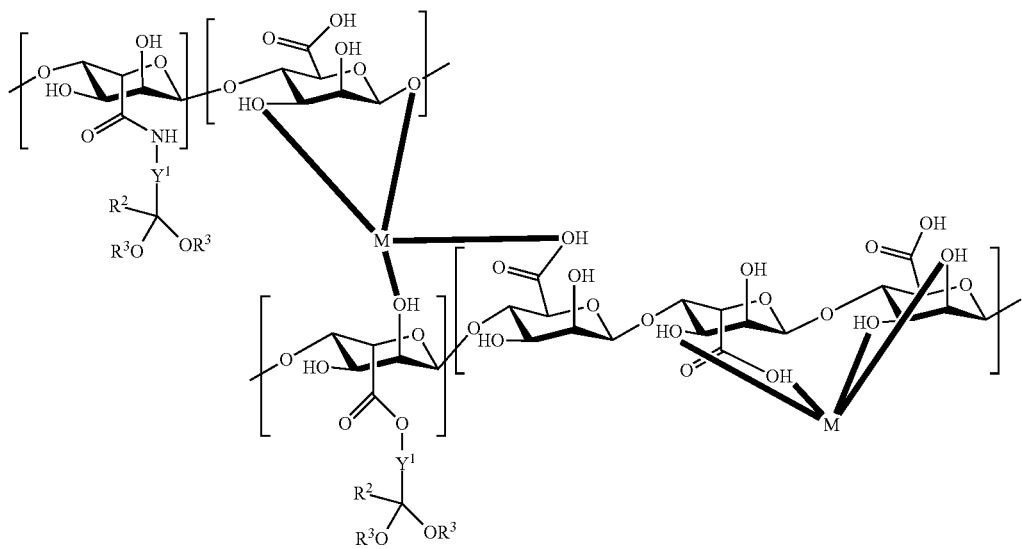

wherein M is a divalent cation, $Y^1$ is an alkanediyl, $R^2$ is optionally substituted alkyl, and each $R^3$ is independently optionally substituted alkyl or an algin monosaccharide residue, provided that at least one of $R^3$ is an algin monosaccharide residue.

The alginoketal is generated in a single step from a naturally-occurring polymer (alginic acid) that is easily obtainable. For example, the alginoketal may be made by forming an alginic acid solution in DI water. 1 to 100 fold stoichiometric excess of 2,2-Bis(aminoethoxy)propane or another compound that contains ketal linkages are added to the alginic acid solution with 100-500 fold stoichiometric excess of crosslinking agents (e.g., sulfo-NHS and EDC)), which leads to the formation of an amide bond. Other crosslinking or catalytic agents leading to the formation of amide are 5-methoxy-2-iodophenylboronic acid (MIBA), XtalFluor-E, Nanosized sulfated titania, T3P (n-propanephosphonic acid anhydride), HBTU, prop-2-ene-1-sulfinyl+DMAP, B(OCH2CF3)3, trimethylaluminium, 3,3-dichlorocyclopropenes among others. The reaction is continued for 24-48 hours at 25-37 degrees C. under stirring. The reaction product is then dialyzed using a filter 500-10000 Da molecular weight cut-off to remove the un-reacted reaction components.

The alginoketal-cation agent may be in any form. For example, cations may be bound to alginoketals by adding a 1-1000 mM solution of cation salt to the 1-100 mL solution of 0.1-10% of alginoketal solution under stirring. The resulting alginoketal-cation polymer may be used as desired. For example, the alginoketal-cation polymer may be coated on a surface to form a hydrogel. Applications may include making the coated surface bacteria resistant, and encapsulating cells.

In certain embodiments, the alginoketal-cation agent is formulated as particle. The alginoketal-cation particles may have any dimension, but typically are microparticles or nanoparticles. For example, the microparticles may have an average size of 1-999 μm or less than 999 μm, more particularly less than 500 μm, and most particularly less than 100 μm. In certain embodiments, the nanoparticles may have an average size 1-999 nm of less than 999 nm, more particularly less than 500 nm, and most particularly less than 250 nm.

The alginoketal-cation particles may be generated by any suitable method. For example, the particles may be generated via a reverse emulsion process. In particular, a 0.1-10% solution of alginoketals in DI $H_2O$ may be generated and used as the water phase. Span 80 (0.1-10 mL) (or another surfactant or mixture of surfactants) can be dissolved in iso-octane (10-1000 mL), and used as the oil phase (other oil phases such as toluene can be used). In order to generate protein encapsulated alginoketal particles, the desired protein (0.001-1000 mg) can be added to the alginoketal solution and vortexed further for thorough mixing. This resulting solution of alginoketals, either containing protein or not containing any protein, may then be added to the oil phase under stirring and allowed to mix. DI $H_2O$ or a cation solution (1-1000 mM) made in DI $H_2O$ can then be added under stirring and allowed to mix. 2-propanol (1-1000 mL) may then be added to the mixture in order to cure the particles, and allowed to mix. The particles obtained may be centrifuged and the supernatant was discarded. The particles can then be re-suspended in 2-propanol, incubated at room temperature and then centrifuged again. The particles can then be re-suspended in 1× phosphate buffered saline and then centrifuged again.

In certain embodiments, the alginoketal can encapsulate an immunotherapeutic agent and/or cancer cytotoxic agent.

In certain embodiments, a protein is encapsulated within the alginoketal Illustrative immunotherapeutic agents for encapsulation include anti-PD-1, anti-PD-L1, anti-CTLA4, anti-Tim3, anti-Lag3, anti-OX40, IL-2, IFN gamma, IFN alpha, anti-CCL22, MPLA, poly(I:C), and CpG.

Illustrative cytotoxic agents for encapsulation include 1-MT.

Alginoketal particles can be produced by different techniques including but not limited to air atomization, emulsification (as described in this embodiment), complexation with counterion polymers (such as chitosan, poly-1-lysine, polyethylene imine among others), spray-drying, electrohydrodynamic atomization, impinging aerosols, precipitation, and inkjet/drying processes.

Uses

In certain embodiments, the alginoketal-M agents disclosed herein may be used for treating or inhibiting a neoplasm. For example, the agents may kill or otherwise inhibit cancer cells, by modulating the intracellular reduction-oxidation potential in the cancer cells, without significantly modifying the potential in non-cancerous cells.

The agents and compositions disclosed herein may be useful for treating any type of neoplasm (e.g., cancer). Tumors or neoplasms include new growths of tissue in which the multiplication of cells is uncontrolled and progressive. Some such growths are benign, but others are termed "malignant," leading to death of the organism. Malignant neoplasms or "cancers" are distinguished from benign growths in that, in addition to exhibiting aggressive cellular proliferation, they invade surrounding tissues and metastasize. Moreover, malignant neoplasms are characterized in that they show a greater loss of differentiation (greater "dedifferentiation"), and of their organization relative to one another and their surrounding tissues. This property is also called "anaplasia."

Illustrative neoplasms include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, multiple myeloma, and lymphoma.

In certain embodiments, the presently disclosed methods are directed to a method for inhibiting cancer growth, including processes of cellular proliferation, invasiveness, and metastasis in biological systems. Preferably, the method is employed to inhibit or reduce cancer cell proliferation, invasiveness, metastasis, or tumor incidence in living animals, such as mammals.

Also provided herein is a method of inducing cytotoxicity (cell killing) in cancer cells or reducing the viability of cancer cells. For example, the methods can be used to induce cytotoxicity in cells of carcinomas of the prostate, breast, ovary, testis, lung, colon, or pancreas.

The killing of cancer cells can occur with less cytotoxicity to normal cells or tissues than is found with conventional cytotoxic therapeutics, preferably without substantial cytotoxicity to normal cells or tissues. For example, the methods identified herein can induce cytotoxicity in cancer cells while producing little or substantially no cytotoxicity in normal cells. Thus, unlike conventional cytotoxic anticancer therapeutics, which typically kill all growing cells, the methods can produce differential cytotoxicity: tumor cells are selectively killed whereas normal cells are spared. Thus, in another embodiment, there is disclosed a method for inducing differential cytotoxicity in cancer cells relative to normal cells or tissue.

In certain embodiments, the alginoketal-M agents disclosed herein may be used for targeting biofilms, and clearing bacteria such as oral biofilms, and biomaterial induced biofilms (heart valves, hip and knee replacements), among others.

In certain embodiments, the alginoketal-M agents disclosed herein may be used for delivery of divalent cations to the brain (e.g., via direct injection into the brain) for brain-related neurodegenerative disorders such as, for example, Alzheimer's disease, ataxia telangiectasia, Parkinson's disease, amyotrophic lateral sclerosis, and Huntington's disease.

In some embodiments, the methods disclosed herein involve administering to a subject in need of treatment a therapeutically effective amount of one or more of the agents disclosed herein. In some embodiments, the methods disclosed herein involve administering to a subject in need of treatment a pharmaceutical composition, for example a composition that includes a pharmaceutically acceptable additive and a therapeutically effective amount of one or more of the agents disclosed herein.

The agents may be administered orally, parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmic ally, rectally, intradermally or intraperitoneally. The pharmaceutical composition may be administered in dosage unit formulations containing conventional non-toxic pharmaceutically acceptable carriers, adjuvants, and/or vehicles. The agents are preferably formulated into suitable pharmaceutical preparations such as tablets, capsules, or elixirs for oral administration or in sterile solutions or suspensions for parenteral administration. Typically the agents described above are formulated into pharmaceutical compositions using techniques and procedures well known in the art.

In some embodiments, one or more of the disclosed agents are mixed or combined with a suitable pharmaceutically acceptable carrier to prepare a pharmaceutical composition. Pharmaceutical carriers or vehicles suitable for administration of the agents provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the agents disclosed herein. In addition, the compounds may be formulated as the sole pharmaceutically active ingredient in the composition or may be combined with other active ingredients.

Upon mixing or addition of the agent(s) to a pharmaceutically acceptable carrier, the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. Where the agents exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the agents, such as salts or prodrugs may also be used in formulating effective pharmaceutical compositions. The disclosed agents may also be prepared with carriers that protect them against rapid elimination from the body, such as time-release formulations or coatings. Such carriers include controlled release formulations, such as, but not limited to, microencapsulated delivery systems.

The disclosed agents and/or compositions can be enclosed in multiple or single dose containers. The agents and/or compositions can also be provided in kits, for example, including component parts that can be assembled for use. For example, one or more of the disclosed agents may be provided in a lyophilized form and a suitable diluent may be provided as separated components for combination prior to use. In some examples, a kit may include a disclosed agent and a second therapeutic agent for co-administration. The compound and second therapeutic agent may be provided as separate component parts. A kit may include a plurality of containers, each container holding one or more unit dose of the agent. The containers are preferably adapted for the desired mode of administration, including, but not limited to, tablets, gel capsules, sustained-release capsules, and the like for oral administration; depot products, pre-filled syringes, ampoules, vials, and the like for parenteral administration; and patches, medipads, creams, and the like for topical administration.

The active agent is included in the pharmaceutically acceptable carrier in an amount sufficient to exert a therapeutically useful effect in the absence of undesirable side effects on the subject treated. A therapeutically effective concentration may be determined empirically by testing the agents in known in vitro and in vivo model systems for the treated disorder. In some examples, a therapeutically effective amount of the agent is an amount that lessens or ameliorates at least one symptom of the disorder for which the compound is administered. Typically, the compositions are formulated for single dosage administration. The concentration of active agent in the drug composition will depend on absorption, inactivation, and excretion rates of the active compound, the dosage schedule, and amount administered as well as other factors known to those of skill in the art.

In some examples, about 0.1 mg to 1000 mg of a disclosed agent, a mixture of such agents, or a physiologically acceptable salt or ester thereof, is compounded with a physiologically acceptable additive such as an excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more agents. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed agent(s).

The disclosed agents or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

When administered orally as a suspension, these compositions are prepared according to techniques well known in the art of pharmaceutical formulation and may contain microcrystalline cellulose for imparting bulk methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the agent is typically provided in a composition that protects it from the acidic environment of the stomach. For example, the composition can be formulated in an enteric coating that maintains its integrity in the stomach and releases the active agent in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active agent can be incorporated with excipients and used in the form of tablets, capsules, or troches.

Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The agents can also be administered as a component of an elixir, suspension, syrup, wafer, chewing gum or the like. A syrup may contain, in addition to the active compounds, sucrose as a sweetening agent and certain preservatives, dyes and colorings, and flavors.

When administered orally, the agents can be administered in usual dosage forms for oral administration. These dosage forms include the usual solid unit dosage forms of tablets and capsules as well as liquid dosage forms such as solutions, suspensions, and elixirs. For example, the dosage unit form may be an injectable fluid, an oral delivery fluid (e.g., a solution or suspension), a nasal delivery fluid (e.g., for delivery as an aerosol or vapor), a semisolid form (e.g., a topical cream), or a solid form such as powder, pill, tablet, or capsule forms.

When the solid dosage forms are used, it is preferred that they be of the sustained release type so that the compounds need to be administered only once or twice daily. In some examples, an oral dosage form is administered to the subject 1, 2, 3, 4, or more times daily. In certain examples, the oral dosage is from about 1 mg/day to about 500 mg/day, about 2 mg/day to about 200 mg/day, or about 5 mg/day to about 50 mg/day. It is understood that while a subject may be started at one dose, that dose may be varied over time as the subject's condition changes.

In additional examples, the agents can be administered orally to humans in a dosage range of 1 to 1000 mg/kg body weight in single or divided doses. One illustrative dosage range is 0.1 to 200 mg/kg body weight orally (such as 0.5 to 100 mg/kg body weight orally) in single or divided doses. For oral administration, the compositions may be provided in the form of tablets containing about 1 to 1000 milligrams of the active ingredient, particularly 1, 5, 10, 15, 20, 25, 50, 75, 100, 150, 200, 250, 300, 400, 500, 600, 750, 800, 900, or 1000 milligrams of the active ingredient. It will be understood, however, that the specific dose level and frequency of dosage for any particular patient may be varied and will depend upon a variety of factors including the activity of the specific agent employed, the metabolic stability and length of action of that compound, the age, body weight, general health, sex, diet, mode and time of administration, rate of excretion, drug combination, the severity of the particular condition, and the host undergoing therapy.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The agents can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The agents can also be administered sublingually. When given sublingually, the agents should be given one to four times daily in the amounts described above for IM administration.

The agents can also be administered intranasally. When given by this route, the appropriate dosage forms are a nasal spray or dry powder. The dosage of the agents for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The agents can be administered intrathecally. When given by this route, the appropriate dosage form can be a parenteral dosage form. The dosage of the compounds for intrathecal administration is the amount described above for IM administration.

The agents can be administered topically. When given by this route, the appropriate dosage form is a cream, ointment, or patch. When administered topically, an illustrative dosage is from about 0.5 mg/day to about 200 mg/day. Because the amount that can be delivered by a patch is limited, two or more patches may be used.

The agents can be administered rectally by suppository. When administered by suppository, an illustrative therapeutically effective amount may range from about 0.5 mg to about 500 mg. When rectally administered in the form of suppositories, these compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

In some cases, it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compound dissolved, partially dissolved, or suspended in one or more pharmaceutically acceptable solvents and can be administered by, for example, a pump or a squeeze-actuated nebulized spray dispenser. The solvents can be, for example, isotonic saline, PBS, or bacteriostatic water. In such embodiments, the pH of the pharmaceutical composition to be administered may be from about 5.0 to about 7.0. The solid composition can be, by way of illustration, a powder preparation including one or more compound or salt, ester, solvate, hydrate, or prodrug thereof described above intermixed with lactose or other inert powders that are acceptable for intrabronchial use, and can be administered by, for example, an aerosol dispenser or a device that breaks or punctures a capsule encasing the solid composition and delivers the solid composition for inhalation, i.e., blister packs. In some embodiments, inhaled compositions encompassed by the invention may include one or more additional inhaled therapeutic compounds. For example, in certain embodiments, the inhaled compositions may include a compound disclosed herein, and one or more additional therapeutic compound such as, for example, bronchodilators such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophylline; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof. The aerosol composition can include, by way of illustration, one or more compound or salt, ester, solvate, hydrate, or prodrug thereof described above, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable. The dosage of the compounds of the invention administered directly to the respiratory system of the patient by, for example, inhalation may be similar to the dosage administered systemically.

In certain embodiments, the compounds or compositions disclosed herein may be administered via intratracheal delivery, with or without co-administration of a bronchodilator such as β2 agonists (SABA/LABA) such as salmeterol, terbutaline, salbutamol, levosalbutamol, pirbuterol, bambuterol, fenoterol, metalproterenol, and formoterol, other bronchodilators such as epinephrine, racemic epinephrine, ephedrine, clenbuterol, indacaterol, vilanterol, and theophyllines; corticosteroids such as beclomethasone, budesonide, ciclesonide, flunisolide, fluticasone and triamcinolone, anticholinergics such as ipratropium and tiotropium, anti-inflammatories such as cromolyn and nedocromil, and the like and various combinations thereof.

In certain embodiments, the alginoketals may be co-administered with another active agent. In certain embodiments, the active agent (particularly a therapeutically active agent) is included in a gel. The gel may respond to external stimulus (e.g., physiological conditions) such as changes in ion concentration, pH, temperature, glucose, shear stress, or a combination thereof. Illustrative gels include hydrogels include polyacrylamide (e.g., poly-N-isopropylacrylamide), silicon hydrogels like those used in contact lenses, polyethylene oxide/polypropylene oxide or combinations of the two (e.g., Pluronics hydrogel or Tectronics hydrogel), butyl methacrylate, polyethylene glycol diacrylate, polyethylene glycol of varying molecular weights, polyacrylic acid, poly methacrylic acid, poly lactic acid, poly(tetramethyleneether glycol), poly(N,N'-diethylaminoethyl methacrylate), methyl methacrylate, and N,N'-dimethylaminoethylmethacrylate. In certain embodiments, the hydrogel is a thermoresponsive hydrogel. Illustrative thermoresponsive gels include poly(N-alkylacrylamides), poly(N-vinyl caprolactam), poly(N-ethyl oxazoline), poly(methyl vinyl ether), poly(acrylic acid-co-acrylamide), elastin-like oligo- and polypeptides.

In certain embodiments, the thermoresponsive hydrogel has a lower critical solution temperature (LCST) below body temperature. The thermoresponsive hydrogel remains fluid below physiological temperature (e.g., 37° C. for humans) or at or below room temperature (e.g., 25° C.), solidify (into a hydrogel) at physiological temperature, and are biocompatible. For example, the thermoresponsive hydrogel may be a clear liquid at a temperature below 34° C. which reversibly solidifies into a gelled composition at a temperature above 34° C. Generally, the LCST-based phase transition occurs upon warming in situ as a result of entropically-driven dehydration of polymer components, leading to polymer collapse. Various naturally derived and synthetic polymers exhibiting this behavior may be utilized. Natural polymers include elastin-like peptides and polysaccharides derivatives, while notable synthetic polymers include those based on poly(n-isopropyl acrylamide) (PNIPAAm), poly(N,N-dimethylacrylamide-co-N-phenylacrylamide), poly(glycidyl methacrylate-co-N-isopropylacrylamide), poly(ethylene oxide)-b-poly(propylene oxide)-b-poly(ethylene oxide), poly(ethylene glycol)-polyester copolymer, poly(ethylene glycol)-poly(serinol hexamethylene urethane), and amphiphilic block copolymers. The structure of PNIPAAm, containing both hydrophilic amide bonds and hydrophobic isopropyl groups, leads to a sharp phase transition at the LCST. Studies suggest that the average number of hydrating water molecules per NIPAAm group falls from 11 to about 2 upon the hydrophobic collapse above the LCST (32-34° C.). In certain embodiments, the amphiphilic block copolymer comprises a hydrophilic component selected from poly ethylene oxide (PEO), poly vinyl alcohol (PVA), poly glycolic acid (PGA), poly (N-isopropylacrylamide), poly (acrylic acid) (PAA), poly vinyl pyrrolidone (PVP) or mixtures thereof, and a hydrophobic component selected from polypropylene oxide (PPO), poly (lactic acid) (PLA), poly (lactic acid co glycolic acid) (PLGA), poly (.beta.-benzoyl L-aspartate) (PBLA), poly (.gamma.-benzyl-L-glutamate) (PBLG), poly (aspartic acid), poly (L-lysine), poly(spermine), poly (caprolactone) or mixtures thereof. Examples of such amphiphilic block copolymers include (PEO)(PPO) (PEO) block copolymers (PEO/PPO), and poly (lactic acid co glycolic acid) block copolymers (PLGA), such as (PEO) (PLGA)(PEO) block copolymers.

In certain embodiments, the hydrogel is non-biodegradable (e.g., PNIPAAm). In other embodiments, the hydrogel is biodegradable. For example, biodegradable NIPAAm-based polymers can be made by conjugating the PNIPAAm with natural biodegradable segments such as MMP-susceptible peptide, gelatin, collagen, hyaluronic acid and dextran. Copolymers formed from NIPAAm and monomers with degradable side chains comprise another category of NIPAAm-based bioabsorbable, thermoresponsive hydrogels. Hydrolytic removal of hydrophobic side chains increases the hydrophilicity of the copolymer, raising the LCST above body temperature and making the polymer backbone soluble. Due to the relative simplicity of the synthetic process, the most investigated biodegradable monomers have been HEMA-based monomers, such as 2-hydroxyethyl methacrylate-polylactide (HEMA-PLA) (Lee, B. H.; et al. Macromol. Biosci. 2005, 5, 629-635; and Guan, J., et al. Biomacromolecules 2008, 9, 1283-92), 2-hydroxyethyl methacrylate-polycaprolactone (HEMA-PCL) (Wang, T., et al. Eur. J. Heart Fail 2009, 11, 14-19 and Wu, D., et al. ACS Appl. Mater. Interf. 2009, 2, 312-327) and 2-hydroxyethyl methacrylate-polytrimethylene carbonate (HEMA-PTMC) (Fujimoto, K. L., et al. Biomaterials 2009, 30, 4357-4368 and Wang, F., et al. Acta Biomater. 2009, 5, 2901). However, the backbone remnant following hydrolysis, HEMA, presents hydroxyethyl side groups (—CH$_2$CH$_2$-OH), which have a relatively limited effect on remnant polymer hydrophilicity (Cui, Z., et al. Biomacromolecules 2007, 8, 1280-1286). In previous studies, such hydrogels have been found to be either partially bioabsorbable (Wu, D., et al. ACS Appl. Mater. Interf. 2009, 2, 312-327) or completely bioabsorbable, but have required the inclusion of considerably hydrophilic co-monomers such as acrylic acid (AAc) in the hydrogel synthesis (Fujimoto, K. L.; et al. Biomaterials 2009, 30, 4357-4368; Wang, F., et al. Acta Biomater. 2009, 5, 2901; and Guan, J., et al. Biomacromolecules 2008, 9, 1283-92).

In a further embodiment, the thermoresponsive hydrogel degrades and dissolves at physiological conditions in a time-dependent manner. The copolymer and its degradation products typically are biocompatible. According to one embodiment, the copolymer consists essentially of N-isopropylacrylamide (NIPAAm) residues (a residue is a monomer incorporated into a polymer), hydroxyethyl methacrylate (HEMA) residues and methacrylate-polylactide (MAPLA) macromer residues as disclosed in U.S. Patent Publ. 2012/0156176, which is incorporated herein by reference. Alternately, the copolymer consists essentially of N-isopropylacrylamide residues, acrylic acid (AAc) residues, and hydroxyethyl methacrylate-poly(trimethylene carbonate) (HEMAPTMC) macromer residues as disclosed in U.S. Patent Publ. 2012/0156176, which is incorporated herein by reference.

Additional biodegradable hydrogels include, but are not limited to, albumin, heparin, poly(hydroxyethylmethacrylate), fibrin, carboxymethylcellulose, hydroxypropylmethyl cellulose, lectin, polypeptides, agarose, amylopectin, carrageenan, chitin, chondroitin, lignin, hylan, α-methyl galactoside, pectin, starch, and sucrose.

The hydrogel may be made from a combination or mixture of any of the hydrogels disclosed herein.

The base precursor (e.g., a prepolymer, oligomer and/or monomer) for the gel, cross linkers, and initiators are mixed together and allowed to polymerize for a predefined period of time (from 1 h to 24 h typically) to form the gel. The gel is then washed to remove any excess initiator or unreacted materials. The gel at this stage is a liquid (e.g., in the form of an aqueous solution) at room temperature until it is ready for use. The active agent can be added in before, after, or during the polymerization of the gel to form a suspension of solid active agent in the gel.

It should be apparent to one skilled in the art that the exact dosage and frequency of administration will depend on the particular agents administered, the particular condition being treated, the severity of the condition being treated, the age, weight, general physical condition of the particular subject, and other medication the individual may be taking as is well known to administering physicians or other clinicians.

Examples

Generation of Alginoketals

A 1 mg/ml alginic acid (MP Biomedical) solution was generated in DI H$_2$O. One (1) molar equivalent of 2,2-Bis (aminoethoxy)propane (Sigma Aldrich) was added with 50 mole excess of Sulfo-NHS (Fisher Scientific) and EDC (Fisher Scientific). The reaction was continued for 16 h at room temperature under stirring. The reaction product was then dialyzed using 500 Da membrane (Spectrum Labs) for 16 h in DI H$_2$O to remove the unreacted EDC, sulfo-NHS and 2,2-Bis(aminoethoxy)propane. The dialyzed product, alginoketal was then lyophilized and analyzed using 1H NMR in D$_2$O at 90° C. (Bruker Avance III 400 MHz).

Generation of Alginoketal Particles

A 10 mg/mL solution of alginoketal in DI H$_2$O was generated by vortexing vigorously and used as the water phase along with 1.25 mL of 30% tween80. Span 80 (1.25 mL; Fisher Scientific) was dissolved in 75 mL of octane (Fisher Scientific), and used as the oil phase. In order to generate protein encapsulated alginoketals, 10 mg of chicken egg white albumin (OVA-Sigma Aldrich) was added to the alginoketal solution and vortexed further for thorough mixing. This solution of alginoketals either containing protein or not containing any protein was then added to the oil phase under stirring at 10,000 rpm (Silverson L4RT-A) and allowed to mix for 3 min. DI H$_2$O or 700 mM CaCl$_2$ solution or Copper (II) sulfate (70 mL; Fisher Scientific) solution made in DI H$_2$O was then added under stirring at 10,000 rpm and allowed to mix for 3 min. 2-propanol (100 mL; Fisher Scientific) was then added to the mixture in order to cure the particles, and allowed to mix for 3 min. The particles obtained were centrifuged (Eppendorf) at 2000×Gs for 5 min and the supernatant was discarded. The particles were then re-suspended in 2-propanol, incubated at room temperature for 5 min and then centrifuged again at 2000×Gs for 5 min. The particles were then re-suspended in 1× phosphate buffered saline (PBS-Fisher Scientific) and then centrifuged again at 2000×Gs for 5 min. The alginoketal particles were then lyophilized and used for further experiments. Alginate particles were made using the same procedure as used for alginoketals.

Size of Alginoketal Particles

Size of alginoketal-Cu and alginoketal-Ca particles was determined using dynamic light scattering (Malvern Instruments Inc., Zetasizer) and found to be 800 nm and 1000 nm respectively. Qualitative analysis of the particle size and shape was performed using scanning electron microscopy (JSM-6330F; JEOL).

pH Degradation of Alginoketals

OVA encapsulated alginoketal particles (1 mg) were incubated in 1×PBS (pH 7.4) for 6 days at 37° C. under circular motion for thorough mixing. The particles were centrifuged at 5,000×Gs for 5 minutes every day and the supernatant was analyzed for the presence of OVA using BCA assay kit (Fisher Scientific). In order to assess the degradation of particles at endosomal pH, 3.33 mg of alginoketal particles were re-suspended in pH 5.6 PBS buffer for 4 hr. The particles were centrifuged at 5,000×Gs for 5 minutes, after 30 min, 1 hr, 2 hr, 3 hr and 4 hr and the supernatant was analyzed for the presence of OVA using BCA assay kit (Fisher Scientific). The total amount of OVA encapsulated in the alginoketal particles was analyzed by dissolving the 1 mg of alginoketal particles in 500 mM EDTA solution in 1×PBS and 100 μL of 1N HCl for 30 min. The amount of OVA in the solution was analyzed using BCA assay kit.

Cell Culture

M05 melanoma cells were cultured in M05 cell media consisting of 1 mg/mL antibiotic G418 (Sigma Aldrich) and 10% fetal bovine serum (FBS-Fisher Scientific), in complete RPMI (Fisher Scientific). M05 cells were passaged every 3$^{rd}$ day using 1× trypsin (Fisher Scientific) and second passage cells were used for all the experiments. HEK293 cells and HeLa cells were cultured in HeLa cell media consisting of 1% penicillin streptomycin, 10% fetal bovine serum in DMEM/F12 (Fisher Scientific), and second passage cells were used for the experiments. HUVEC cells were cultured in 5 ng/mL EGF, 1% penicillin streptomycin, 10% fetal bovine serum in RPMI media, and second passage cells were used for the experiments. MSC cells were cultured in 1% penicillin streptomycin, 1% anti-anti and 10% fetal bovine serum in α-MEM media and $1^{st}$ passage was used for the experiments.

Endosome Disruption by Alginoketal Particles

M05 cells were seeded in the wells of the 96-well plate (Fisher Scientific) at $10^4$ cells per well for 16 h. alginoketal-Ca (100 μg/mL) or alginate particles (100 μg/mL) were incubated with 4 μM calcein (Sigma-Aldrich) with M05 cells for 15 min. Calcein is a membrane impermeable dye and has been used for evaluating membrane integrity. Calcein at 4 μM without the addition of particles was utilized as control. The cells were washed 3 times with 200 μL 1×PBS and imaged with a fluorescent microscope (Nikon). Images were obtained via bright field and FITC filters of the same field using a 20× objective and overlapped images were generated using ImageJ software.

Depletion of Superoxides Generated Via Fenton's Reaction by Alginoketal-Cu

The ability of alginoketal-Cu to deplete the superoxides generated were assessed by adding 50 μL of 100 μg/mL, 50 μg/mL, 25 μg/mL, 12.5 μg/mL, 6.25 μg/mL, 3.125 μg/mL, 1.5625 μg/mL alginoketal-Cu or alginoketal-Ca to 10 μL of 0.1 mM $FeCl_3$ (Sigma Aldrich) made in DI $H_2O$ to the wells of a 96 well plate. Stabilized tetramethylbenzidine substrate (50 μL; Color reagent B, R&D systems) was added immediately and the absorbance was measured using the plate reader (Molecular Devices, SpectraMax M5) at 650 nm.

Generation of Hydrogen Peroxide by Alginoketal-Cu

The ability of alginoketal-Cu to generate hydrogen peroxide was assessed by incubating 100 μg/mL, 50 μg/mL, 25 μg/mL, 12.5 μg/mL, 6.25 μg/mL, 3.125 μg/mL, 1.5625 μg/mL alginoketal-Cu or alginoketal-Ca with 1 mM $KO_2$ (Sigma Aldrich) for 1 h. Stabilized tetramethylbenzidine substrate (50 μL; Color reagent B, R&D systems) and 1 ng/mL horseradish peroxidase (Sigma Aldrich) was then added to assess the levels of remaining superoxides and the absorbance was measured using the plate reader (Molecular Devices, SpectraMax M5) at 650 nm after 30 min of incubation.

Cell Death Using Alginoketal-Cu

HeLa, HEK293, M05, MSC and HUVEC cells ($10^4$) were seeded in the wells of a 96-well plate for 16 h. Alginoketal-Cu or alginoketal-Ca (100 μg/mL) or 1×PBS was added to the cells and incubated for 16 h. Live/dead assay was then performed using live/dead assay kit (Life Technologies) and percentage of live cells were determined.

The effect of different concentrations of alginoketal-Cu on M05 cell death was also determined. M05 cells ($10^4$) were seeded in the wells of a 96 well plate for 16 h. Alginoketal-Cu was re-suspended in M05 cell media, and added to a final concentration of 100 μg/mL, 50 μg/mL, 25 μg/mL or 10 μg/mL of alginoketal-Cu for 16 h. Alginoketal-Ca (100 μg/mL) and cells treated without any particles, were utilized as negative controls. Cells were then washed twice with 1×PBS, and live assay was performed using live/dead assay kit (Life Technologies). The percentage of live cells was determined by normalizing all the conditions with the negative control of no particle treatment control.

Intracellular Hydrogen Peroxide Levels Generated by Alginoketal-Cu

In order to determine intracellular hydrogen peroxide levels in M05 cells, dihydrodichlorofluorescein diacetate (DCF, Sigma Aldrich) was utilized. M05 cells ($10^4$) were seeded in the wells of the 96 well plate for 16 h. Alginoketal-Cu (100 μg/mL, 50 μg/mL, 25 μg/mL or 10 μg/mL) were added to the cells for 1 h. Alginoketal-Ca (100 μg/mL) and cells treated without any particles, were utilized as negative controls. The cells were washed twice with 1×PBS and 25 μM DCF made in dimethyl sulfoxide (DMSO-Fisher Scientific) was added, in order to get a final concentration of 5 μM DCF in the cell culture. The cells were incubated with DCF for 10 min at 37° C., and the fluorescence was determined at excitation/emission 488/540 nm using the plate reader. In a separate set of experiments, the same procedure was performed for DCF staining, and the cells were imaged using the FITC filter via a fluorescent microscope at 10× objective.

Statistical Analysis

Statistical analyses were performed using a student t-test and p-values for each experiment were determined.

Figure 6B:
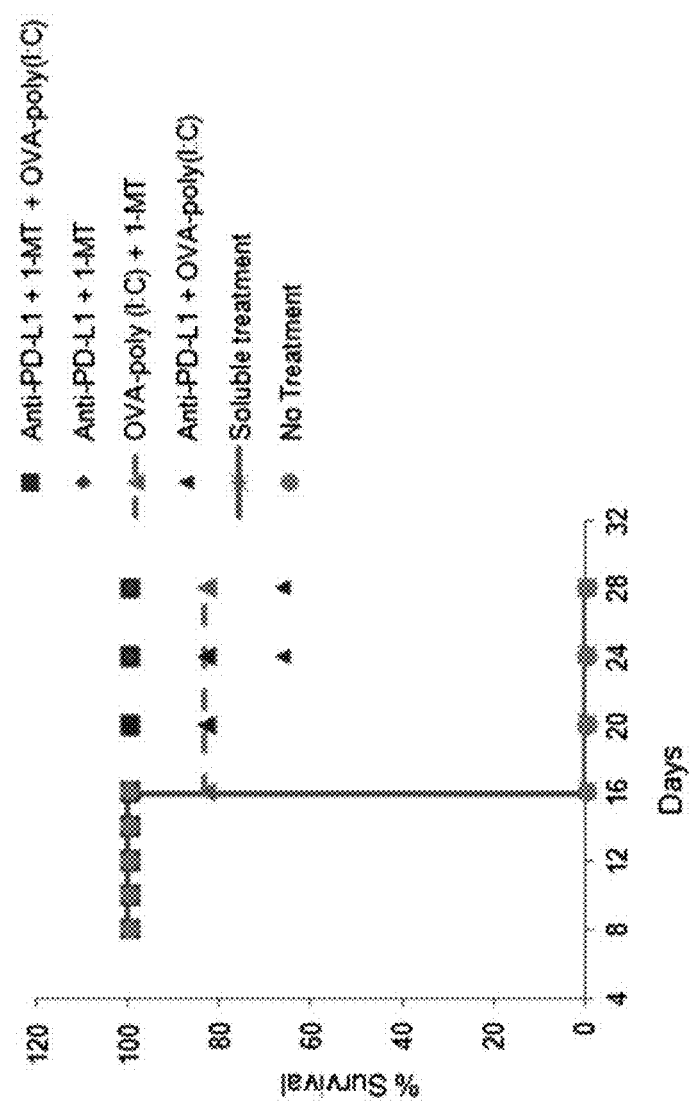
FIGS. 6A-6D. Stapled acid-sensitive endosome disrupting alginates modulate survival in mice and tumor growth.
Figure 6A:
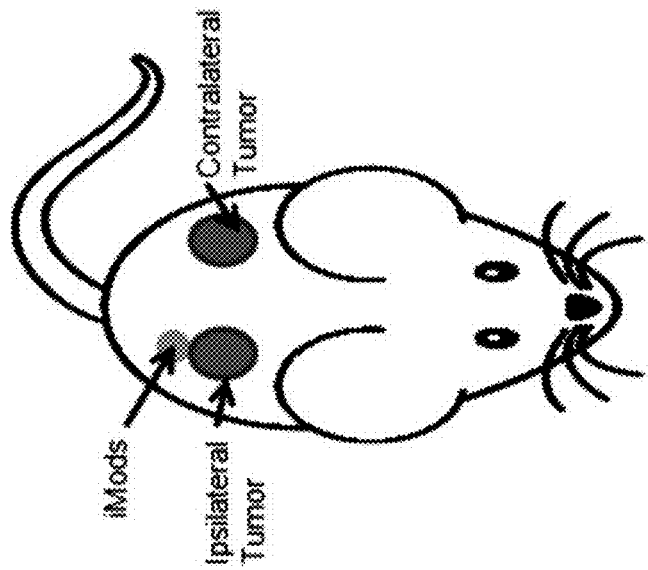
Figure 6D:
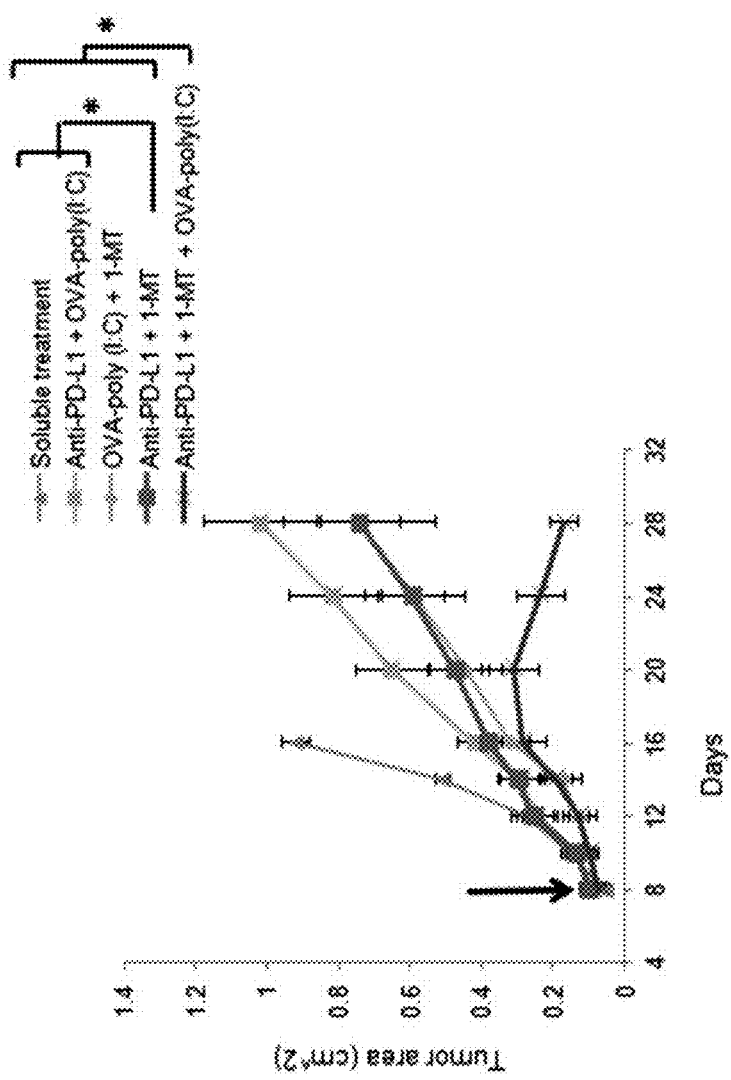
Figure 6C:
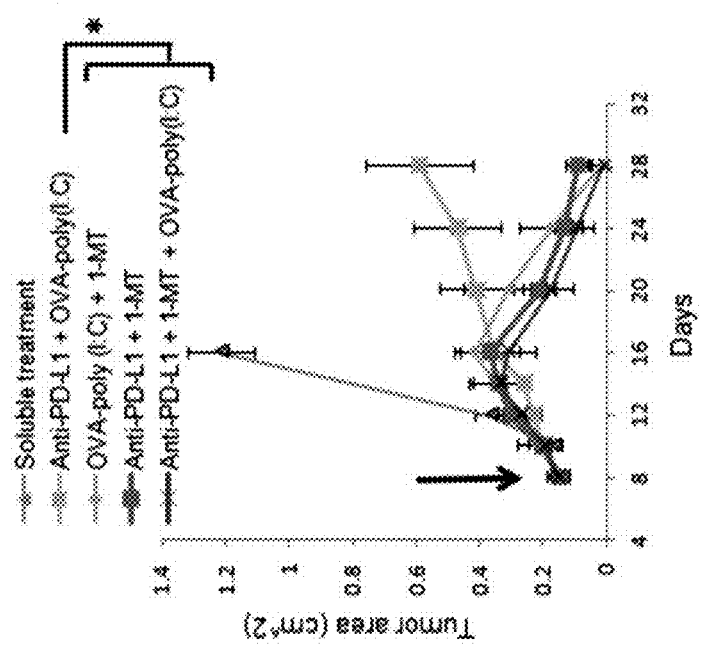

FIGS. 6A-6D. Stapled Acid-Sensitive Endosome Disrupting Alginates Modulate Survival in Mice and Tumor Growth. (FIG. 6A)

"Soluble treatment"—Soluble delivery of antibody against PD-L1 (programmed death ligand 1), soluble delivery of 1-MT (1 methyl tryptophan), soluble delivery of OVA (chicken egg white albumin) and soluble delivery of poly I:C. These soluble delivery pertains to injection of these components.

"Anti-PD-L1+OVA-poly(I:C)"—Antibody against PD-L1 incorporated in a thermoresponsive gel called poly (ethylene glycol)-poly(serinol hexamethylene urethane), however other thermoresponsive material can be utilized+OVA and poly(I:C) encapsulated in alginoketal-Ca particles. The active agent-loaded, thermoresponsive gel and alginoketal-Ca particles were mixed together and injected in mice.

"OVA-poly(I:C)"—OVA and poly(I:C) encapsulated in alginoketal-Ca particles. Alginoketal-Ca particles were injected in mice.

"Anti-PD-L1+1-MT"– Antibody against PD-L1 incorporated in a thermoresponsive gel called poly(ethylene glycol)-poly(serinol hexamethylene urethane), however other thermoresponsive material can be utilized+1-MT encapsulated in alginoketal-Ca particles. The active agent-loaded thermoresponsive gel and alginoketal-Ca particles were mixed together and injected in mice.

"Anti-PD-L1+1-MT+OVA-poly(I:C)"—Antibody against PD-L1 incorporated in a thermoresponsive gel called poly(ethylene glycol)-poly(serinol hexamethylene urethane), however other thermoresponsive material or no thermoresponsive gel can be utilized+OVA and poly(I:C) encapsulated in alginoketal-Ca particles+1-MT encapsulated in alginoketal-Ca particles. The active agent-loaded thermoresponsive gel and alginoketal-Ca particles were mixed together and injected in mice.

Alginoketal particles were generated using an inverse emulsion method. Alginoketal particles were generated with tween 80 (1.25 mL of 30% v/v in DI $H_2O$—Fisher Scientific), Span 80 (1.25 mL; Fisher Scientific, Pittsburgh, Pa.), 5 mL of 10 mg/mL solution of alginoketals in DI $H_2O$ and 75 mL of iso-octane (Fisher Scientific, Pittsburgh, Pa.). In order to generate OVA-poly(I:C) or 1-MT encapsulated alginoketal particles, 10 mg of chicken egg white albumin (OVA-Sigma Aldrich, St. Louis, Mo.)+10 mg of poly(I:C) (Sigma Aldrich, St. Louis, Mo.) or 50 mg of 1-MT were added to the alginoketal solution and vortexed further for thorough mixing. This solution of alginoketals along with tween 80 were then added to the iso-octane solution under stirring at 10,000 rpm (Silverson L4RT-A, East Longmeadow, Mass.) and allowed to mix for 3 min. Next, 700 mM $CaCl_2$ solution (70 mL; Fisher Scientific, Pittsburgh, Pa.) solution made in DI $H_2O$ was added under stirring at 10,000 rpm and allowed to mix for 3 min. 2-propanol (100 mL; Fisher Scientific, Pittsburgh, Pa.) was then added to the mixture in order to cure the particles, and allowed to mix for 3 min. The particles obtained were centrifuged at 1800×Gs for 1 min and the supernatant was discarded. The particles were then re-suspended in 2-propanol, incubated at room temperature for 5 min and then centrifuged again. The alginoketal particles were then lyophilized and used for further experiments.

Results

Figure 2A:
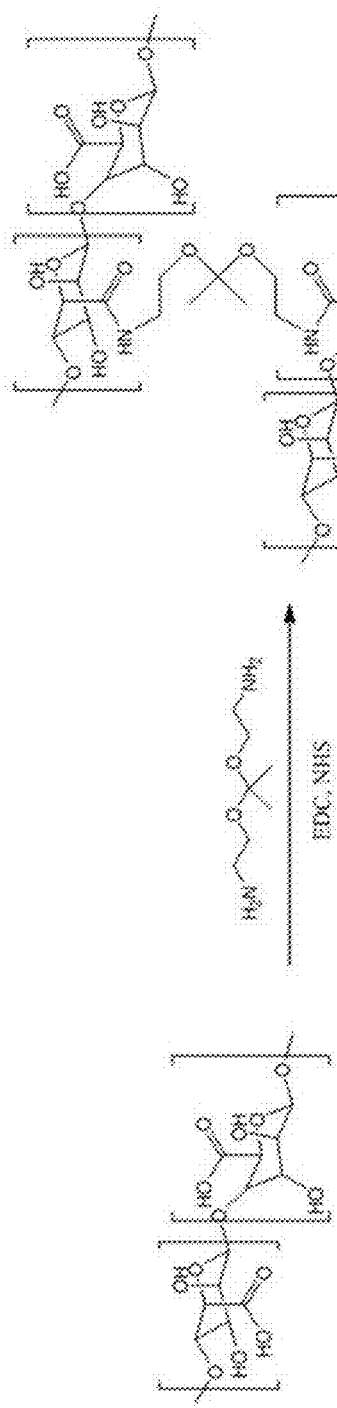
FIGS. 2A-2C: Alginoketals were generated by crosslinking alginate and bis-amino ketals. A) The scheme of the reaction between alginic acid and bis-amino ketal. B) 1H NMR was obtained for the alginoketals and shows the peaks of bis-amino ketal and alginate. C) The FTIR analysis showed that the shift in the peak of carboxylic acid vibrations from 1595 in alginate to 1620 in alginoketals suggests the formation of an amide bond.
Figure 2B:
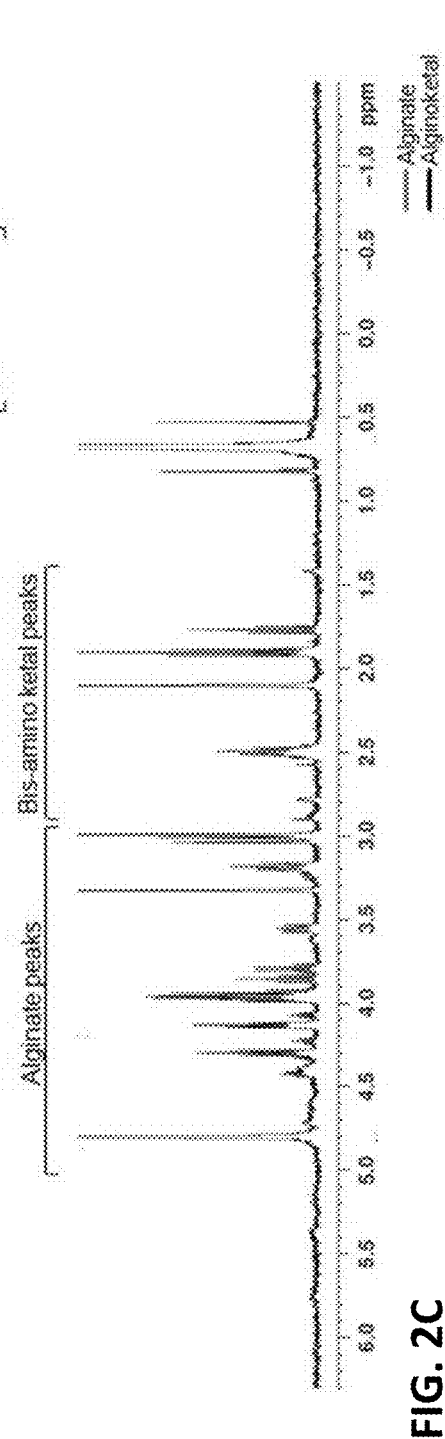
Figure 2C:
Figure 3A:
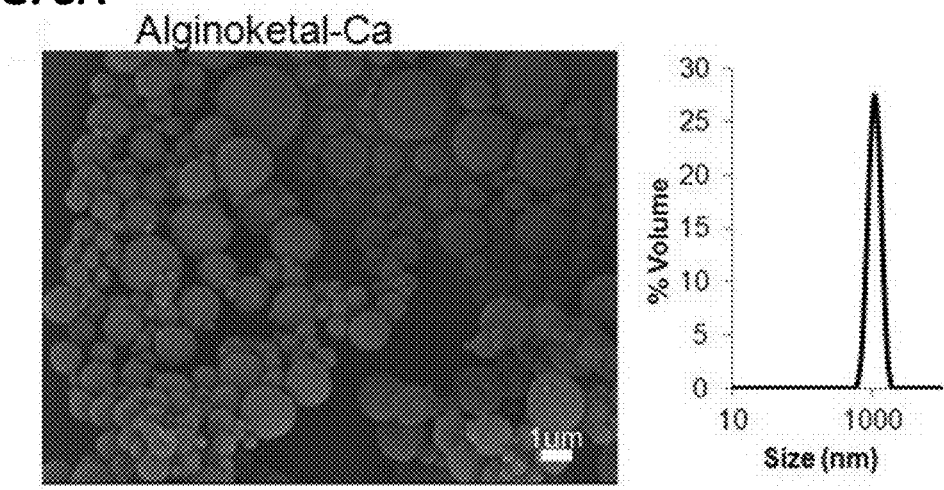
FIGS. 3A-3D: Size of the alginoketal particles generated using inverse emulsion. A) Alginoketal particles with Ca as the binding agent were generated and characterized using SEM and DLS, and there average size was 1 μm. B) Alginoketal particles with Cu as the binding agent were generated and characterized using SEM and DLS, and their size was approximately 0.8 μm. C) Alginoketal particles were incubated at pH 7.4 for 6 days and the amount of OVA released was measured. The figure shows that at pH 7.4 alginoketal particles release only 20% of the encapsulated OVA. D) Alginoketal particles were incubated at pH 5.6 for 4 hours and the OVA released was quantified. At pH 5.6 Alginoketal particles released 100% of the encapsulated OVA within 2 hr.
Figure 3B:
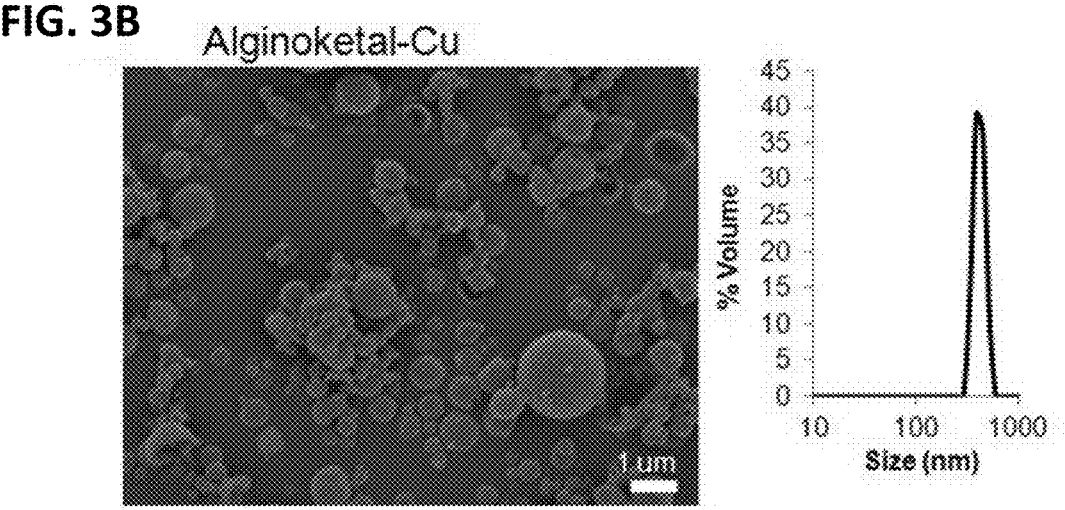

Alginoketals were generated by conjugating naturally occurring alginic acid with bis-amino ketals, via a straightforward amide forming reaction, using 1-Ethyl-3-[3-dimethylaminopropyl]carbodiimide hydrochloride (EDC) and sulfo-N-hydroxysulfosuccinimide (sulfo-NHS) (FIG. 2A). The generation of Alginoketals was confirmed using 1H NMR (FIG. 2B) and FTIR (FIG. 2C), where the formation of the amide bond was confirmed by the shift in the carboxylic acid peak from 1595 in alginate to 1620 in alginoketals. Nanoparticles were generated from Alginoketals using inverse emulsions, and Ca or Cu was used as a binding agent. Although, the particles were poly-disperse as seen in the scanning electron microscopy and dynamic light scattering experiments, all particle populations measured remained in the endocytosable size range (FIG. 3A,B).

Figure 3C:
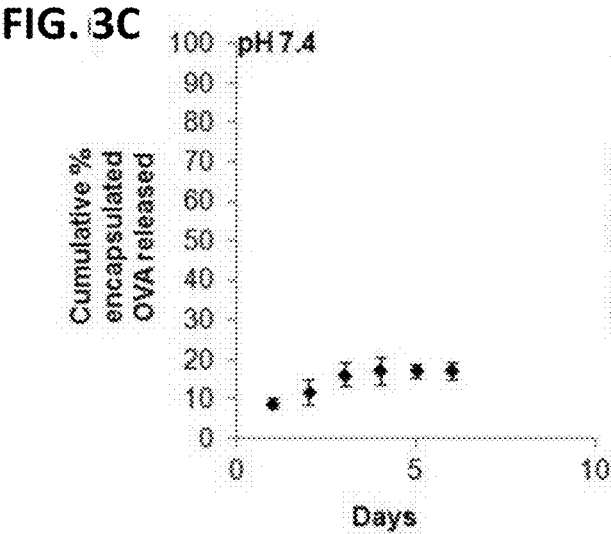
Figure 3D:
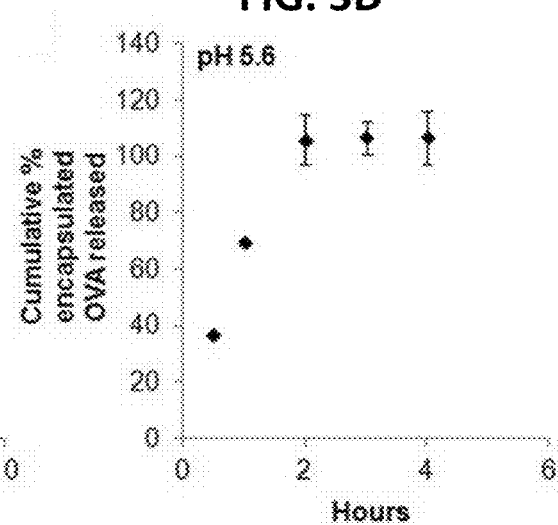

In order to deliver divalent cations to the cytosol, an endocytosable particle should be capable of disrupting endosomes (pH-5). Therefore, alginoketals were generated using ketal linkages that are known to hydrolyze at pH 5. Hydrolysis of the ketals then can induce endosome disruption, and release the divalent cations and encapsulated materials in the cytosol of the cells. The effect of pH on Alginoketals was tested by encapsulating a model protein chicken egg white ovalbumin (OVA) and determining its release kinetics at endosomal pH 5.6 and physiological pH 7.4. We observed that at pH 5.6 Alginoketal particles hydrolyzed and released 100% of the encapsulated OVA within 2 hr (FIG. 3D), whereas at pH 7.4, only 20% of the OVA was released after 6 days (FIG. 3C).

Figure 4A:
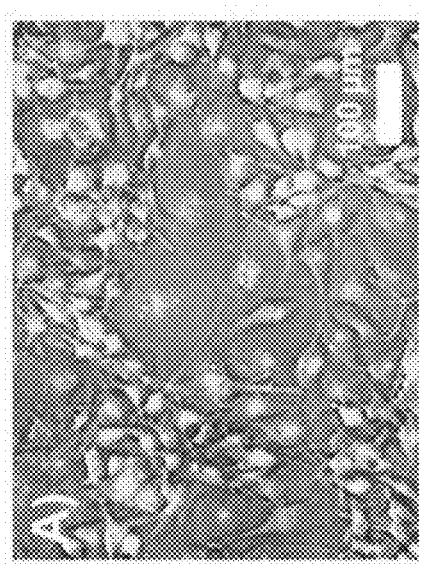
FIGS. 4A-4C: Alginoketal particles are endosome disruptors. A) M05 cells were incubated with alginoketal-Ca particles and calcein for 15 min. The fluorescence shown here in green in the cytosol of the cells, demonstrates that alginoketal particles disrupted the endosomes of M05 and delivered calcein to the cytosol. B) M05 cells were incubated with alginate particles and calcein for 15 min. The absence of fluorescence in the cytosol of the cells, demonstrates that alginate particles could not disrupted the endosomes of M05 cells. C) M05 cells were incubated with calcein for 15 min. The absence of fluorescence in the cytosol of the cells, demonstrates that calcein by themselves do not reach the cytosol of the M05 cells.
Figure 4B:
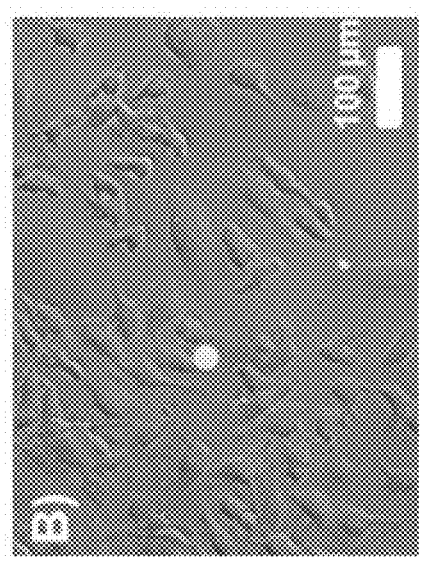
Figure 4C:
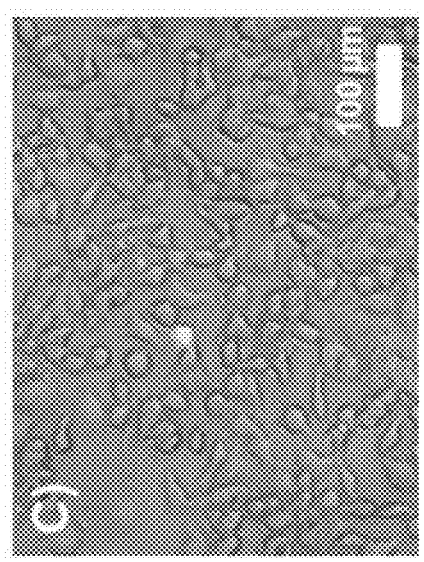

The endosome disrupting ability of the Alginoketals was tested by incubating Alginoketal particles and membrane impermeable calcein dye with M05 (B16F10-OVA expressing) cell lines. Alginoketals appear capable of delivering calcein to the cytosol of M05 cells within 15 min of co-incubation (FIG. 4A), whereas poly (lactide-co-glycolide) particles generated via water in oil emulsion were not able to deliver calcein to the cytosol even after 1 h of incubation (FIG. 4B).

Figure 5A:
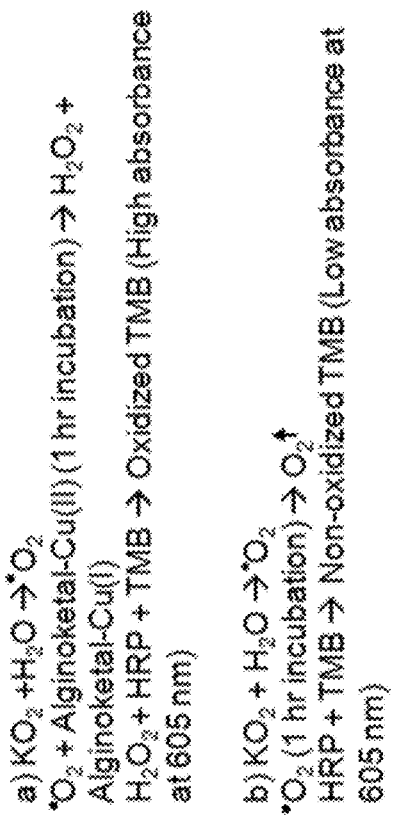
FIGS. 5A-5H: Cell death due to hydrogen peroxide accumulation in M05 melanoma cancer cell due to alginoketal-Cu. A,B) Alginoketal-Cu particles scavenge radical oxygen, thereby preventing the oxidation of TMB substrate, whereas alginoketal-Ca particles were not able to scavenge the radical oxygen. C,D) Alginoketal-Cu particles may act like superoxide dismutase and were able to generate hydrogen peroxide from radical oxygen as determined by the oxidation of TMB in the presence of hydrogen peroxide and horseradish peroxidase, whereas the negative control Alginoketal-Ca particles did not induce hydrogen peroxide production. E) Alginoketal-Cu particles at 100 μg/mL induced higher cell death in cancer cell types (M05 and HeLa) as compared to non-cancerous cell types (MSCs, HUVECs and HEK293). F) Addition of alginoketal-Cu particles induce cell death in M05 melanoma cancer cells in a dose dependent manner, as determined by live/dead assay after 16 h of incubation with Alginoketal-Cu or Alginoketal-Ca particles. G) Alginoketal-Cu particles induced intracellular production of hydrogen peroxide in the M05 cells in a dose-dependent manner, as observed by the oxidation of DCF, after 1 h of incubation. H) Qualitative observation of alginoketal-Cu particles induced hydrogen peroxide in M05 cells as observed by intracellular fluorescence due to hydrogen peroxide production, after 1 h of incubation with Alginoketal-Cu particles and M05 cells. i) 100 μg/mL Alginoketal-Cu particles ii) 50 µg/mL Alginoketal-Cu particles iii) 25 µg/mL Alginoketal-Cu particles iv) 10 µg/mL Alginoketal-Cu particles v) 100 µg/mL Alginoketal-Ca particles vi) No treatment.
Figure 5B:
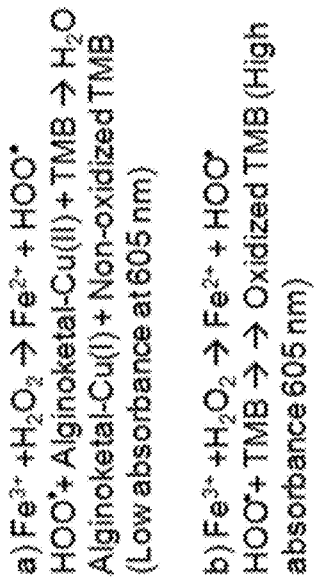
Figure 5C:
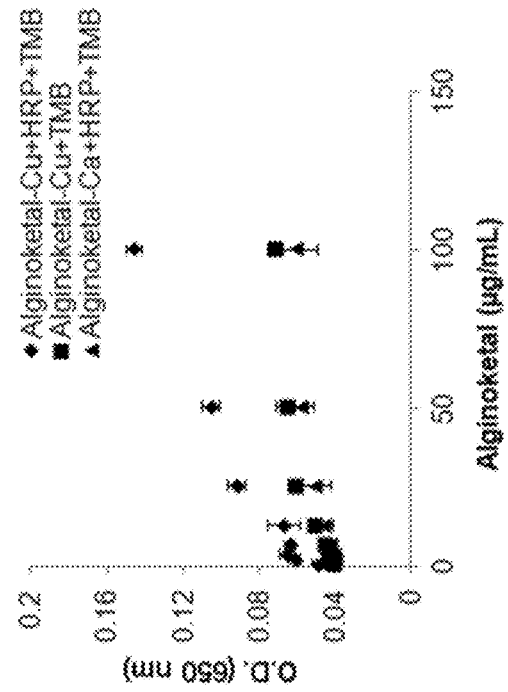
Figure 5D:
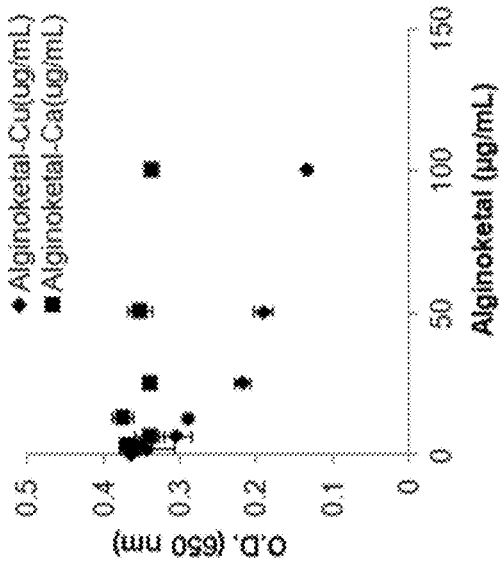

In order to demonstrate that Alginoketal-Cu can act as the superoxide dismutase mimic and scavenge superoxide radicals, we incubated Alginoketal-Cu with superoxide radicals generating $FeCl_3$. Alginoketal-Cu (50 μL) at various concentrations were added to 50 μL of 0.1 mM $FeCl_3$ and 50 μL tetramethylbenzidine (TMB) substrate. The change in absorbance at 650 nm was measured immediately and lower levels of absorbance represented scavenging of the superoxide radicals (FIG. 5A). It was observed that Alginoketal-Cu were able to scavenge the radicals generated by $FeCl_3$ in a dose dependent manner (FIG. 5B). In order to further elucidate the role of Alginoketal-Cu as a superoxide dismutase mimic, we determined if Alginoketal-Cu could convert superoxides into hydrogen peroxide. Excess cytosolic Cu(II) is known to induce the production of hydrogen peroxide, via Cu (II) to Cu (I) reactions in the presence of superoxide (FIG. 5C), which then leads to cell death (12, 18). The ability of Alginoketal-Cu to produce hydrogen peroxide in the presence of superoxide was assessed by incubating varying concentrations of Alginoketal-Cu with 1 mM $KO_2$ for 1 h. Tetramethylbenzidine and horseradish peroxidase were then added in order to determine the levels of hydrogen peroxide generated by Alginoketal-Cu. FIG. 5D demonstrates that the absorbance at 650 nm corresponding to the level of hydrogen peroxide is directly correlated with the amount of Alginoketal-Cu, which shows that Alginoketal-Cu were able to induce the production of hydrogen peroxide in a dose dependent manner.

Figure 5E:
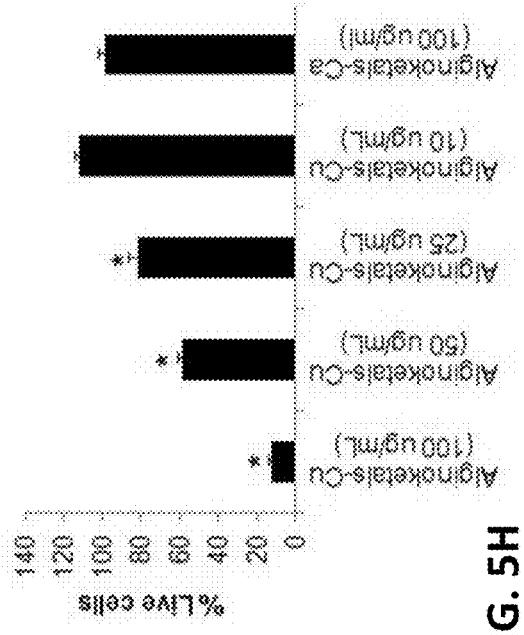
Figure 5F:
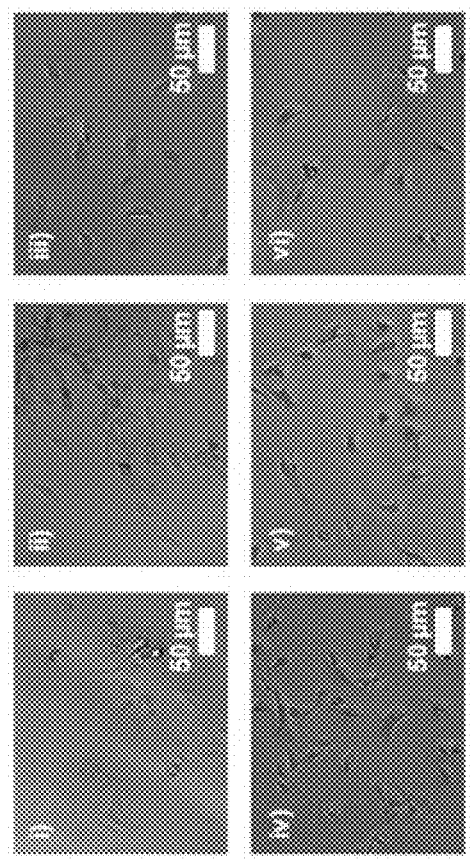
Figure 5G:
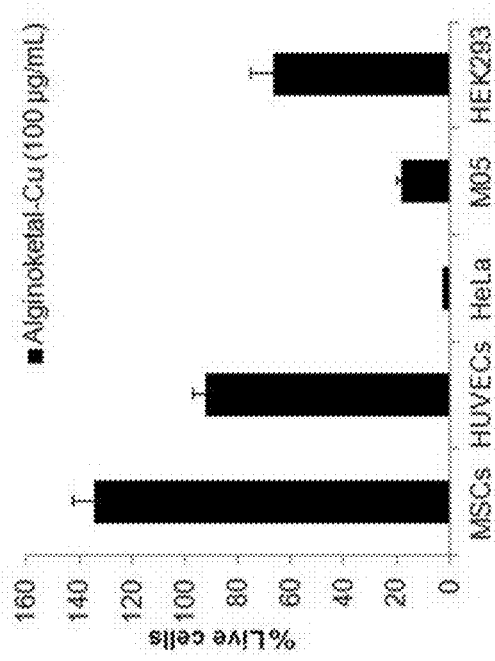
Figure 5H:
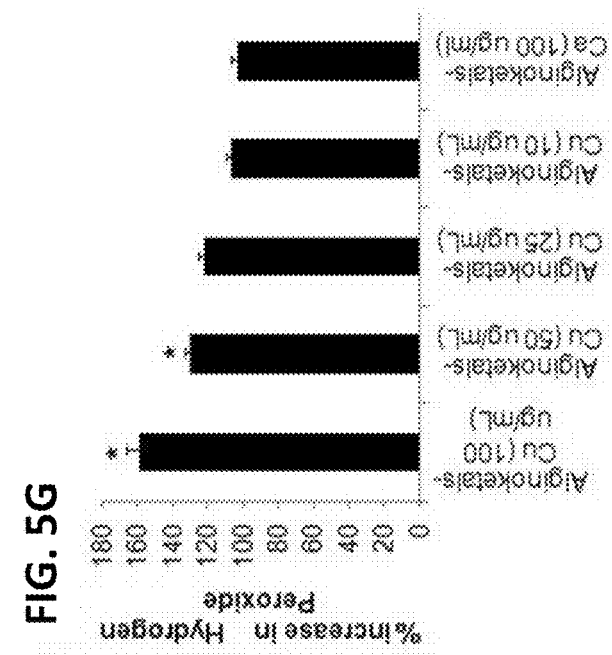

In order to demonstrate that Alginoketals can deliver Cu(II) cations and modulate the reactive oxygen species homeostasis in the cytosol of the cells, we generated Cu containing Alginoketals (Alginoketal-Cu) and incubated them with M05 melanoma cancer cells. Mammalian cells are excellent at maintaining cytosolic Cu homeostasis via the expression of copper transporters and therefore, prevent cell death due to Cu toxicity (19, 20). In this report, we demonstrate that intracellular Cu levels can be increased in M05 cancer cells using Alginoketal-Cu, which lead to increased hydrogen peroxide levels and cell death. We also compared the effects of Alginoketal-Cu on cancerous and non-cancerous cells. Alginoketal-Cu (100 μg/mL) were incubated with non-cancerous cells (MSCs, HEK293 and HUVECs) and cancerous cells (M05 and HeLa) overnight and their effect on cell death was observed. We observed that Alginoketal-Cu preferentially induced cell death in cancerous cells as compared to non-cancerous cell types (FIG. 5E). Different levels of Alginoketal-Cu were incubated with the M05 cells for 16 h and percentage live cells were determined. FIG. 5F shows that the Alginoketal-Cu appear to be capable of inducing cell death at 100 μg/mL, 50 μg/mL and 25 μg/mL, whereas 10 μg/mL levels of Alginoketal-Cu does not induce cell death. These data suggest that low levels of Cu support cell growth whereas higher levels of Cu induce cell death. In order to determine if Cu induced the production of hydrogen peroxide, M05 cells were seeded in 96-well plate and incubated with 100 μg/mL, 50 μg/mL, 25 μg/mL, and 10 μg/mL levels of Alginoketal-Cu or 100 μg/mL of Alginoketal-Ca for 1 h. The amount of hydrogen peroxide generated, normalized to no treatment control shows that 100 μg/mL, 50 μg/mL and 25 μg/mL levels of Alginoketal-Cu induced significantly higher amounts of intracellular hydrogen peroxide in cancer cells as compared to 100 μg/mL Alginoketal-Ca, which might lead to cell death (FIG. 5G). The accumulation of hydrogen peroxide by Alginoketal-Cu in M05 cells was qualitatively assessed via fluorescent microscopy (FIG. 5H), which shows that higher levels of alginoketal-Cu lead to induction of larger amount of intracellular accumulation of hydrogen peroxide in M05 cells.

In view of the many possible embodiments to which the principles of the disclosed invention may be applied, it should be recognized that the illustrated embodiments are only preferred examples of the invention and should not be taken as limiting the scope of the invention.

What is claimed is:

1. An agent comprising:
    an algin monosaccharide residue covalently bonded to an acetal group forming an alginoketal; and
    at least one cation coupled to the alginoketal, wherein the at least one cation is Cu(II).

2. The agent of claim 1, wherein the cation is chelated to the alginoketal.

3. The agent of claim 1, wherein the agent includes at least one additional type of cation.

4. The agent of claim 3, wherein the least one additional cation is selected from iron, calcium, zinc, magnesium, selenium, aluminum, manganese, barium, strontium or a combination thereof.

5. The agent of claim 1, wherein the at least one additional type of cation is calcium.

6. The agent of claim 1, further comprising a protein encapsulated within the alginoketal.

7. The agent of claim 1, further comprising an immunotherapeutic agent or a cancer cytotoxic agent encapsulated within the alginoketal.

8. A particle comprising the agent of claim 1.

9. A composition comprising a plurality of the particles of claim 8.

10. The composition of claim 9, wherein the particles have an average particle size of 1 nm to 10,000 µm.

11. A pharmaceutical composition comprising the agent of claim 1 and at least one pharmaceutically acceptable additive.

12. A pharmaceutical composition comprising the composition of claim 9.

13. A pharmaceutical composition comprising the agent of claim 1, and an active agent-loaded thermoresponsive gel.

14. The particle of claim 8, wherein the particle encapsulates an immunotherapeutic agent, a cancer cytotoxic agent, or both an immunotherapeutic agent and a cancer cytotoxic agent.

15. The particle of claim 8, wherein the particle encapsulates a protein.

16. The agent of claim 1, wherein a single cation is coupled to the alginoketal.

17. A method for increasing the intracellular level of at least one cation above homeostatic level in a cell, comprising contacting the cell in a subject in need thereof with the agent of claim 1.

18. A method for increasing the intracellular level of at least one cation above homeostatic level in a cell, comprising contacting the cell with the composition of claim 9.

19. A method comprising delivering at one cation to the cytosol of a cell, comprising contacting the cell with the agent of claim 1.

20. A method comprising delivering at one cation to the cytosol of a cell, comprising contacting the cell with the composition of claim 9.

21. A method comprising delivering at least one cation to the cytosol of a prokaryotic or eukaryotic cell, comprising contacting the cell with the agent of claim 1.

* * * * *

UNITED STATES PATENT AND TRADEMARK OFFICE
CERTIFICATE OF CORRECTION

PATENT NO. : 10,967,066 B2
APPLICATION NO. : 16/450553
DATED : April 6, 2021
INVENTOR(S) : Acharya et al.

Page 1 of 1

It is certified that error appears in the above-identified patent and that said Letters Patent is hereby corrected as shown below:

In the Claims

Column 40, Line 15, Claim 19, "A method comprising delivering at one cation to the cytosol of a cell," should read --A method comprising delivering at least one cation to the cytosol of a cell--

Column 40, Line 18, Claim 20, "A method comprising delivering at one cation to the cytosol of a cell," should read --A method comprising delivering at least one cation to the cytosol of a cell--

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*